(12) United States Patent
Shaikh

(10) Patent No.: US 12,102,982 B2
(45) Date of Patent: *Oct. 1, 2024

(54) METHOD FOR MAKING NATURAL MATERIAL-SUPPORTED PALLADIUM CATALYST

(71) Applicant: KING FAHD UNIVERSITY OF PETROLEUM AND MINERALS, Dhahran (SA)

(72) Inventor: M. Nasiruzzaman Shaikh, Dhahran (SA)

(73) Assignee: KING FAHD UNIVERSITY OF PETROLEUM AND MINERALS, Dhahran (SA)

(*) Notice: Subject to any disclaimer, the term of this patent is extended or adjusted under 35 U.S.C. 154(b) by 0 days.

This patent is subject to a terminal disclaimer.

(21) Appl. No.: 18/606,569

(22) Filed: Mar. 15, 2024

(65) Prior Publication Data

US 2024/0269652 A1  Aug. 15, 2024

Related U.S. Application Data

(60) Continuation of application No. 17/929,166, filed on Sep. 1, 2022, now Pat. No. 11,980,870, which is a division of application No. 16/732,579, filed on Jan. 2, 2020, now Pat. No. 11,471,861.

(51) Int. Cl.
| | | |
|---|---|---|
| B01J 23/44 | (2006.01) |
| B01J 31/06 | (2006.01) |
| B01J 35/30 | (2024.01) |
| B01J 35/40 | (2024.01) |
| B01J 37/04 | (2006.01) |
| B01J 37/08 | (2006.01) |
| B01J 37/16 | (2006.01) |
| C07C 1/26 | (2006.01) |

(52) U.S. Cl.
CPC .............. *B01J 23/44* (2013.01); *B01J 31/06* (2013.01); *B01J 35/393* (2024.01); *B01J 35/40* (2024.01); *B01J 37/04* (2013.01); *B01J 37/08* (2013.01); *B01J 37/16* (2013.01); *C07C 1/26* (2013.01); *B01J 2231/4211* (2013.01); *B01J 2231/4261* (2013.01); *C07C 2523/44* (2013.01)

(58) Field of Classification Search
CPC . B01J 35/393; B01J 35/40; B01J 31/06; B01J 37/04; B01J 37/08; B01J 37/16; C07C 1/26

See application file for complete search history.

(56) References Cited

U.S. PATENT DOCUMENTS

| | | | |
|---|---|---|---|
| 7,776,777 B2 | 8/2010 | Kim | |
| 8,835,345 B2 | 9/2014 | Moores et al. | |
| 11,980,870 B2 * | 5/2024 | Shaikh | ............... C07C 2/861 |

FOREIGN PATENT DOCUMENTS

| | | | |
|---|---|---|---|
| CN | 102274753 A | * | 12/2011 |
| CN | 104984759 B | | 12/2017 |
| CN | 106622327 B | | 1/2019 |
| CN | 108543547 B | | 6/2019 |
| CN | 110090663 A | | 8/2019 |

OTHER PUBLICATIONS

U.S. Appl. No. 18/606,656, filed Mar. 15, 2024, Shaikh; M. Nasiruzzaman.*
U.S. Appl. No. 18/606,738, filed Mar. 15, 2024, Shaikh; M. Nasiruzzaman.*
Mohammed Nasiruzzaman Shaikh, et al., "PdNPs@ZIF-8 Micro-Nanostructured Catalyst of Regioselective Mizoriki-Heck Olefination", ChemistrySelect, vol. 2, Issue 28, Oct. 5, 2017, pp. 9052-9057 (Abstract only).
Zayneb Jebali, et al., "Cationic cellulose nanofibrils as a green support of palladium nanoparticles: catalyst evaluation in Suzuki reactions", Callulose, vol. 25, Issue 12, Dec. 2018, pp. 6963-6975.
Pengyao Ju, et al., "Salen-porphyrin-based conjugated microporous polymer supported Pd nanoparticles: highly efficient heterogeneous catalysts for aqueous C—C coupling reactions", Journal of Materials Chemistry A, vol. 7, Issue 6, Jan. 4, 2019, pp. 2660-2666 (Abstract only).
Ciprian M. Cirtiu, et al., "Cellulose nanocrystallites as an efficient support for nanoparticles of palladium: application for catalytic hydrogenation and Heck coupling under mild conditions", Green Chemistry, vol. 13, 2011, pp. 288-291.
A. C. Chakravarty, "Measurement of Density of Fibers of Jute by Density Gradient Column", Journal of Polymer Science, vol. 54, Issue 160, Oct. 1961, pp. S52-S56.
Zheng et al., J. of Phys. Chem. Lett., (2015), v.6, p. 230-238.
Natural fibers and their composites, (2008), "1.6.5 Thermogravimetric analysis of jute fibers" at pp. 28-30.

* cited by examiner

*Primary Examiner* — Yong L Chu
(74) *Attorney, Agent, or Firm* — Oblon, McClelland, Maier & Neustadt, L.L.P.

(57) ABSTRACT

A solid-supported Pd catalyst is suitable for C—C bond formation, e.g., via Suzuki-Miyaura and Mizoroki-Heck cross-coupling reactions, with a support that is reusable, cost-efficient, regioselective, and naturally available. Such catalysts may contain Pd nanoparticles on jute plant sticks (GS), i.e., Pd@GS, and may be formed by reducing, e.g., $K_2PdCl_4$ with $NaBH_4$ in water, and then used this as a "dip catalyst." The dip catalyst can catalyze Suzuki-Miyaura and Mizoroki-Heck cross coupling-reactions in water. The catalysts may have a homogeneous distribution of Pd nanoparticles with average dimensions, e.g., within a range of 7 to 10 nm on the solid support. Suzuki-Miyaura cross-coupling reactions may achieve conversions of, e.g., 97% with TOFs around 4692 $h^{-1}$, Mizoroki-Heck reactions with conversions of, e.g., a 98% and TOFs of 237 $h^{-1}$, while the same catalyst sample may be used for 7 consecutive cycles, i.e., without addition of any fresh catalyst.

15 Claims, 29 Drawing Sheets

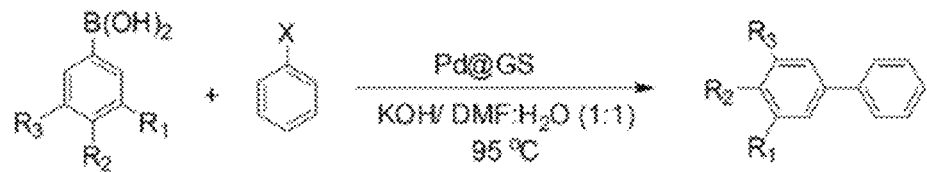

| Entry | Catalyst | Substrate (R1,R2,R3) | Halide (X) | Base | Solv. | Temp. (°C) | Time (min) | Conv. (%) | TOF (h⁻¹) |
|---|---|---|---|---|---|---|---|---|---|
| 1 | Pd@GS | H,H,H | I | $K_2CO_3$ | $H_2O$ | 90 | 90 | 92 | 1483 |
| 2 | | | | $Na_2CO_3$ | $H_2O$ | 90 | 90 | 91 | 1467 |
| 3 | | | | $NaHCO_3$ | $H_2O$ | 90 | 90 | 87 | 1402 |
| 4 | | | | TEA | $H_2O$ | 90 | 180 | 82 | 661 |
| 5 | | | | KOH | $H_2O$ | 90 | 60 | 95 | 2298 |
| 6 | | | | KOH | DMF | 90 | 60 | 67 | 1620 |
| 7 | | | | KOH | Tol | 90 | 60 | 54 | 1306 |
| 8 | | | | KOH | $H_2O$:EtOH | 90 | 60 | 90 | 2177 |
| 9 | | | | KOH | $H_2O$ | 50 | 300 | 57 | 276 |
| 10 | Pd@GS | H,H,H | Br | KOH | $H_2O$ | 90 | 60 | 59 | 1427 |
| 11 | | | Cl | KOH | $H_2O$ | 90 | 120 | 45 | 544 |
| 12 | Pd@GS | H,Ac,H | I | KOH | $H_2O$ | 90 | 30 | 97 | 4692 |
| 13 | | | Br | KOH | $H_2O$ | 90 | 60 | 75 | 1814 |
| 14 | | | Cl | KOH | $H_2O$ | 90 | 90 | 57 | 919 |
| 15 | Pd@GS | Me,H,Me | I | KOH | $H_2O$ | 90 | 30 | 95 | 4595 |
| 16 | | Me,H,Me | Br | KOH | $H_2O$ | 90 | 60 | 89 | 2153 |
| 17 | | Me,H,Me | Cl | KOH | $H_2O$ | 90 | 90 | 54 | 971 |
| 18 | GS | H,H,H | I | KOH | $H_2O$ | 90 | 30 | nd | - |
| 19 | $PdCl_2$ | H,H,H | I | KOH | $H_2O$ | 90 | 30 | 99 | 4789 |
| 20 | $Pd(PPh_3)_4$ | H,H,H | I | KOH | $H_2O$ | 90 | 30 | 99 | 4789 |
| 21 | Pd/C | H,H,H | I | KOH | $H_2O$ | 90 | 30 | 99 | 4789 | a one strip (2 cm) and 1 mmol of boronic acid were used; b solvent ratio 1:1 in case of mixture of solvent; c measured by GC and identified by GC-MS.

Fig. 5

| S. No. | Catalyst system | Reaction condition | Conv. (%) | TOF (h⁻¹) |
|---|---|---|---|---|
| 1 | Pd@PANI | K₂CO₃, 95 °C, dioxane·H₂O | 91 | 10 |
| 2 | Pd@NHC | Cs₂CO₃, DMF, 100 °C | 99 | 3 |
| 3 | Pd@AuNPs | K₂CO₃, EtOH-H₂O, 80 °C | 88 | 1 |
| 4 | Pd-Schiff-base@MCM-41 | K₂CO₃, PEG, 100 °C | 91 | 51 |
| 5 | Pd@CA | K₂CO₃, H₂O, 100 °C | 94 | 94 |
| 6 | Pd@Polymer | K₂CO₃, DMF:H₂O(1:1), 80 °C | 99 | 40 |
| 7 | Pd@SBA-15 | K₂CO₃, H₂O, 80 °C | 97 | 129 |
| 8 | Pd-MPA@MCM-41 | K₂CO₃, PEG, 100 °C | 95 | 28 |
| 9 | Pd-imi@MCM-41/Fe₃O₄ | Na₂CO₃, PEG, 80 °C | 98 | 118 |
| 10 | Pd@GS | KOH, H₂O, 90 °C | 95 | 2298 |

Fig. 7

| Serial No | Catalyst system | Base | Solvent | Temp. (°C) | Conv. (%) |
|---|---|---|---|---|---|
| 1 | Pd(0)-MCM-41 | NaOAC | DMF | 100 | 56 |
| 2 | NHC-Pd | NaOAC | DMF | 140 | 87 |
| 3 | Pd(OAc)$_2$ | K$_3$PO$_4$ | DMAc | 140 | 98 |
| 4 | POM-IL-Pd | TEA | DMF | 100 | 49 |
| 5 | Pd-TPA/ZrO2 | K$_2$CO$_3$ | DMF | 120 | 59 |
| 6 | Pd-MIL-53 (Al) | TEA | DMF | 120 | 93 |
| 7 | Pd@GS | KOH | DMF:H$_2$O | 90 | 97 |

Fig. 8

METHOD FOR MAKING NATURAL MATERIAL-SUPPORTED PALLADIUM CATALYST

CROSS REFERENCE TO RELATED APPLICATIONS

The present application is a Continuation of U.S. application Ser. No. 17/929,166, now U.S. Pat. No. 11,980,870, having a filing date of Sep. 1, 2022 which is a Divisional of U.S. application Ser. No. 16/732,579, now U.S. Pat. No. 11,471,861, having a filing date of Jan. 2, 2020. The present application is related to U.S. application Ser. No. 16/715,782 titled "Jute Stem-Supported Palladium and Use as Dip-Catalysts for Aqueous Transfer Hyrogenation" (U.S. Pat. No. 11,446,636), filed on Dec. 16, 2017, which is incorporated herein by reference.

STATEMENT OF ACKNOWLEDGEMENT

The inventors gratefully acknowledge the support from the National Plan for Science, Technology, and Innovation (MAARIFAH)-King Abdulaziz City for Science and Technology through the Science and Technology Unit at King Fahd University of Petroleum and Minerals (KFUPM), Kingdom of Saudi Arabia, award number 15-NAN4650-04.

STATEMENT REGARDING PRIOR DISCLOSURES BY INVENTOR(S)

Aspects of the present disclosure are described in "Pd nanoparticles on green support as dip-catalyst: a facile transfer hydrogenation of olefins and N-heteroarenes in water," which was authored by the inventor and published online in RSC Adv. 2019, 9, 28199-28206, on Sep. 9, 2019, which is incorporated herein by reference in its entirety.

BACKGROUND OF THE INVENTION

Field of the Invention

The present disclosure relates to catalysts, particularly dip catalysts, including Pd and/or other noble metals, using a "green" support of renewable material comprising cellulose and lignin, particularly from jute stem or "stick," and typically having support dimensions of 0.1 or more millimeters.

Description of the Related Art

Catalysis based on transition metals plays a significant role in the production of industrial chemicals. Of all of the organic transformations, aromatic carbon-carbon bond formation reactions have attracted a good deal of attention due to their role in achieving complex organic syntheses, for example, of polymers, pharmaceuticals, dyes and other compounds. Moreover, C—C coupling reactions, particularly aromatic C—C coupling reactions, using transition metals can be tolerant of the presence of diverse organic functional groups such as carbonyl, hydroxyl, nitro, and cyano groups, and of unsaturated double or triple bonds, and can proceed under mild reaction conditions. Most of these C—C bond formation reactions have been reported to be mediated by Pd or Pd complexes.

The frequently high catalytic activity of Pd has been attributed to the facile interchange between Pd(II) and Pd(IV) or Pd(0) and Pd(II) species. Efforts have been made to develop a homogeneous phosphine-ligand-based Pd system, which have borne useful results, but the preparation of the highly air-sensitive and moisture-sensitive phosphines and related ligands is tedious and cumbersome. Recently, the catalytic use of Pd nanoparticles has been applied to organic functional group transformations including the Suzuki, Mizoroki-Heck, Sonogashira, Stille, Negishi, and Hiyama reactions. Since typical palladium or platinum-based catalytic systems involve an extensive usage of toxic chemicals, complicated multistep syntheses, and restricted reusability, it would be desirable to use a catalytic system that is more environmentally benign, and/or in which the catalyst is more easily separated from the product.

Immobilizing the catalyst onto a porous solid support is one approach to making catalysts more environmentally friendly and commercially viable. A number of reports have been published in the art on such catalysts, supported on zeolite, silica, polymer, alumina, metal organic frameworks (MOFs), carbon nanotubes, and magnetic nanoparticles. However, these conventional architectures suffer from serious drawbacks, including difficulties in reducing the diffusion of the substrate towards active particles and reactants and in preventing the leaching of metal from the solid surface.

Recently, "dip catalysts" have gained interest in catalysis research due to their frequently improved efficiency in terms of turn-over frequency (TOF), ease of fabrication, and reusability. Furthermore, the often facile insertion of dip catalysts into and remove from reaction solutions can be useful in industrial contexts. Dip catalysts for use in Suzuki-Miyaura cross-coupling reactions have been reported. For example, a case using immobilized Pd nanoparticles on filter paper reportedly demonstrated efficiency and recyclability for the cross-coupling reactions. A further example used a Pd nanoparticle-based 'dip catalyst' in a Suzuki-Miyaura reaction to produce a quantitative conversion with a high reaction rate and reusability. In another reported case, metallic nanoparticles were attached onto cellulose acetate and efficiently utilized for a C—C bond formation reaction in an aqueous medium. Further research in the art warrants mention.

CN 104984759 B to Wang et al. (Wang) discloses a nanometer cellulose supported nanometer palladium catalyst and its preparation. Wang's Pd loading is 0.04-4 wt. % relative to the cellulose. Wang's preparation involves: oxidizing nano-cellulose into nano-aldocellulose; reacting the nano-aldocellulose with a palladium chloride solution to prepare the nano-cellulose supported nano-palladium. Wang's catalyst is stable and catalytically active for the Suzuki reaction of aryl bromides, but Wang's catalyst has a nanometer-sized support (no more than 100 nm), and Wang's support has only cellulose.

CN 110090663 A by Wu et al. (Wu) discloses a method for improving the water phase reaction circulation of a bacterial cellulose-plant fiber composite paper-based catalyst. Similarly, CN 108543547 B to Xiang et al. (Xiang) discloses a catalytic test paper produced by compounding bacterial cellulose-supported metal particles with plant fibers, containing nitrogen or phosphorus. Wu's method involves adding a dispersant and a fiber cross-linking agent to compound bacterial cellulose loaded with metal nanoparticles and plant fibers, to improve the water phase reaction recycling of the paper-based catalyst. Wu and Xiang may use cellulose secreted and synthesized by bacterial microorganisms and metals such as Au, Cu, Ag, Pd, Cr, Ni, and other metals with catalytic properties. Wu's dispersant may be carboxymethyl cellulose, xylan, glucomannan, cationic etherified starch, polyethylene oxide, or the like. Wu uses a fiber crosslinking agent, which may be epichlorohydrin, polyethyleneimine, polyacrylamide, polyvinyl alcohol, polyamide, or the like. Aside from requiring a nitrogen or phosphorus-containing cellulose, Wu and Xiangs's catalyst supports lack lignin.

U.S. Pat. No. 8,835,345 to Moores et al. (Moores) discloses a catalyst comprising metal nanoparticles supported on nanocrystalline cellulose and a homogeneous catalyst system comprising this catalyst colloidally suspended in a fluid, as well as methods of making and using this catalyst. Moores's metal may comprise Pd, Ni, Ru, Pt, and/or Ag, have a diameter of 2 to 10 nm, and be 0.5 to 5 wt. % of the cellulose, which cellulose may be form of whiskers having a length ranging from 100 to 300 nm and a width of 5 to 15 nm. Moores's cellulosic material may be synthesized by acid hydrolysis of wood pulp, and its catalysts may be suitable for C—C couplings. Moores's cellulose is nanocrystalline, e.g., CNCs that are nano-bundles, or nano-whiskers, generally of ~100 to 250 nm long by 3 to 10 nm. Moores does not mention jute, let alone jute stems.

CN 106622327 B to Chen et al. (Chen) discloses a catalyst composed of 0.1 to 30 wt. % of metal particles and 70 to 99.9 wt. % of bio-N-doped porous carbon carrier, useful for catalyzing aqueous phase hydrogenation of biofurfural to selectively prepare furfural alcohol or cyclopentanone. Chen's metal may be Pd, Au, Ag, Pt, Rh, Ru, and/or Ir. Chen's nitrogen-doped porous carbon may be prepared from sweet potato leaves, glutinous rice, dandelion leaves, yellow flower seedling leaves, jute leaves, burdock leaves, asparagus, bamboo shoots, white cauliflower, spinach, or broccoli. However, Chen does not describe lignin-containing materials, or jute stems, as a catalyst support. Chen fails to disclose C—C coupling reactions.

*Chem. Select* 2017, 2(28), 9052-9057 by Shaikh et al. (Shaikh) discloses a heterogeneous catalyst comprising zeolite imidazolate framework (ZIF-8) supported palladium nanoparticles (PdNPs@ZIF-8) for the Mizoriki-Heck C—C coupling reactions. Shaikh reports hexagonal ZIF-8 microcrystals forming rod- and flower-shaped PdNPs@ZIF-8 by controlled addition of formic acid. Shaikh does not describe cellulosic and/or lignin-containing support materials, such as jute stem, nor dip catalysts.

*Cellulose* 2018, 25, 6963-6975 by Jebali et al. (Jebali) discloses cationic cellulose nanofibrils (C-CNF) as a support for growth and immobilization of Pd NPs using $PdCl_2$. Jebrali uses the Pd@C-CNF nanocomposite as a catalyst for Suzuki coupling reactions between aryl halides (e.g., 4-bromoacetophenone) and arylboronic acid (e.g., phenyl boronic acid) in DMF. Jebali reports easy removability and reuse of Pd@C-CNF for three Suzuki reaction cycles without significant loss of its catalytic activity or leaching of the loaded Pd. Jebali uses a modified cellulosic material, without describing any lignin content, derived from *Ammophila arenaria* (marram) grass, and fails to describe jute stem or similar materials.

*J. Mater. Chem. A* 2019, 7, 2660-2666 by Ju et al. (Ju) discloses salen-porphyrin based-conjugated microporous polymer (SP-CMP), constructed by polycondensation reaction of a salen-dialdehyde derivative and pyrrole, to give ordered salen-porphyrin arrays in an A4B4-type polymer framework as a Pd nanoparticle support. Ju reports a BET surface area of 266 $m^2/g$ and a pore volume of 0.192 $cm^3/g$ for its Pd@SP-CMP. Ju reports that the Pd@SP-CMP material with dispersed Pd nanoparticles has catalytic activity towards Suzuki-Miyaura and Heck-Mizoroki coupling reactions in water or in dioxane/water mixtures. Ju reports stability and recyclability for its Pd@SP-CMP, including reused without loss of activity in ten successive reactions. Ju does not describe a cellulose-containing and/or lignin-containing support, much less from jute or jute stems.

*Green Chem.* 2011, 13, 288-291 by Cirtiu et al. (Cirtiu) discloses the synthesis of a hybrid material, PdNPs@CNCs of monodisperse Pd nanoparticles (PdNPs) deposited onto colloidal cellulose nanocrystallites (CNCs). Cirtiu reports activity for hydrogenating phenol to cyclohexanone in water, at room temperature, under 4 bar of $H_2$. Cirtiu's catalyst can Heck couple styrene and iodobenzene in a hydro-organic mixture, and the CNCs are crystalline, ordered, and obtainable from wood pulp. Cirtiu's cellulose nanocrystallites are small in scale, and Cirtiu describes no lignin in its support.

In light of the above, a need remains for new catalytic systems, particularly containing green materials and/or larger support platforms, suitable for facile retrieval from reaction mixtures, and capable of catalyzing C—C bond formation including via Heck and/or Suzuki coupling, while operating in or around ambient conditions and in environmentally tolerable solvents such as water or mixtures thereof, and methods of making and using such catalysts.

SUMMARY OF THE INVENTION

Aspects of the invention provide C—C coupling catalysts, comprising: a solid support matrix particles comprising at least 75 wt. % of α-cellulose, hemicellulose, and lignin, based on total support weight; and a catalytic metal comprising palladium disposed on the solid support matrix, wherein the palladium is present in an amount of from 0.01 to 1 wt. % relative to a total catalyst weight, and wherein the solid support matrix particles have an average longest dimension of at least 1 μm. Such catalysts may be modified by any permutation of features described herein, particularly the following.

The solid support matrix particles may have no average dimension less than 100 μm. The α-cellulose, hemicellulose, and lignin, may be from jute stems. The solid support matrix particles may comprise 20 to 60 wt. % α-cellulose, based on the total support weight. The solid support matrix particles may comprise 10 to 35 wt. % lignin, based on the total support weight. The solid support matrix particles may comprise 10 to 30 wt. % hemicellulose, based on the total support weight. The solid support matrix particles may comprise 30 to 50 wt. % α-cellulose, 15 to 30 wt. % lignin, and 15 to 25 wt. % hemicellulose, based on the total support weight. The support matrix particles may comprise at least 90 wt. % jute stems, based on the total support matrix weight.

The palladium may be in the form of nanospheres and/or have an average particle size of from 2.5 to 45 nm or 5 to 15 nm. The catalyst may comprise at least 90 wt. % of the palladium, relative to total metal weight in the catalyst. At least 90 at. % of the palladium may in elemental state.

Aspects of the invention provide methods of preparing solid-supported palladium catalysts, which methods may comprise: mixing a particulate matrix, comprising α-cellulose, hemicellulose, and lignin, with a palladium ion in an aqueous solution to form a suspension; combining the suspension with a reducing agent to form a mixture; and/or heating the mixture to thereby reduce at least 50 wt. % of the palladium ions, relative to total catalytic metal weight, and form the solid-supported palladium catalyst, wherein the particulate matrix comprises particles have no average dimension less than 10 μm.

The reducing agent may comprise a borohydride, such as NaBH$_4$. The palladium compound may comprise palladium ion comprises a [PdCl$_4$]$^{2-}$ anion, such as K$_2$PdCl$_4$.

The heating may comprise treating the mixture at a temperature in a range of from 40 to 100° C. The heating may be conducted for a duration in the range of from 10 to 60 minutes.

Aspects of the invention provide processes of catalyzing a cross-coupling reaction, which processes may comprise: reacting an aryl halide with an optionally substituted aryl boronic acid, or an optionally substituted alkene in the presence of any permutation of the inventive catalyst described herein, and a base and/or a solvent.

The cross-coupling reaction may be a Suzuki-Miyaura reaction. The base may be potassium hydroxide and/or the solvent comprises water. The cross-coupling reaction may be a Mizoroki-Heck reaction. The base may be potassium hydroxide. The solvent may comprise water and dimethylformamide.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5 shows a table presenting data on reaction conditions and efficiencies of an exemplary Pd@GS catalyst material in the catalysis of Suzuki-Miyaura cross-coupling reactions of substituted boronic acids with aryl halides in water in various conditions;

FIG. 7 shows a table presenting data on reaction conditions and efficiencies of an exemplary Pd@GS catalyst material in the catalysis of the Suzuki-Miyaura cross-coupling reaction of iodobenzene with phenylboronic acid with previously reported literature values;

FIG. 8 shows a table presenting data on reaction conditions and efficiencies of an exemplary Pd@GS catalyst material in the catalysis of the Mizoroki-Heck cross-coupling reaction of styrene and arylbromide with previously reported literature values;

DETAILED DESCRIPTION OF THE INVENTION

Figure 1:
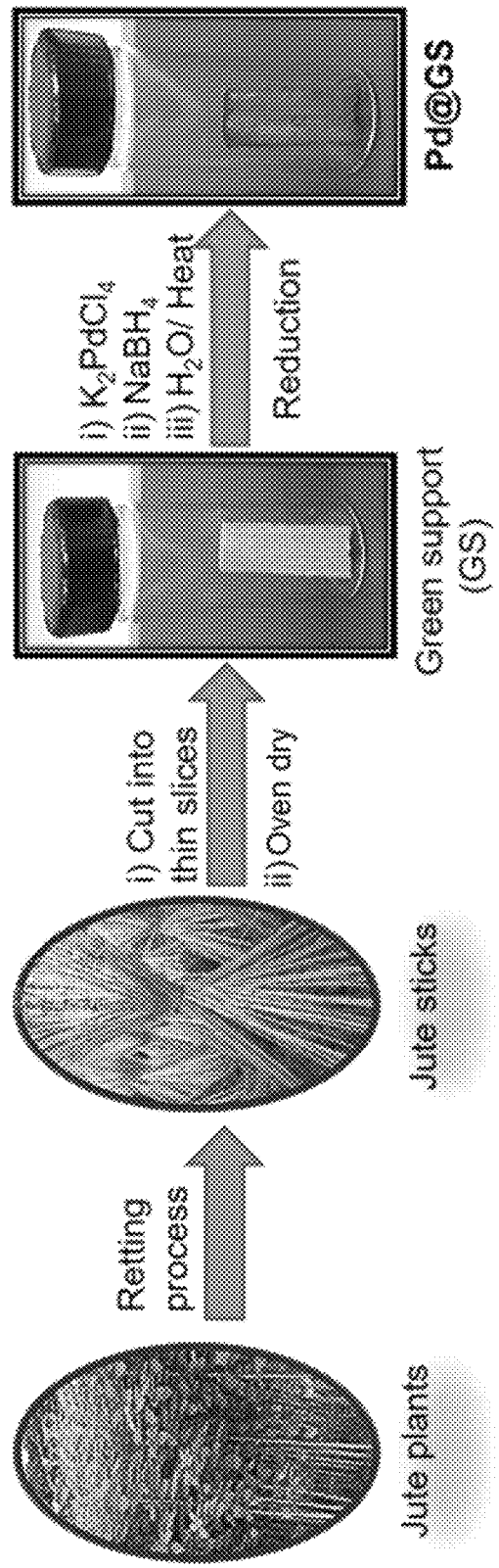
FIG. 1 shows a schematic illustration of an exemplary synthesis of a palladium on jute stick "green support" (GS), i.e., Pd@GS.

Aspects of the invention provide C—C coupling catalysts, i.e., catalysts capable of catalyzing the formation of carbon-carbon bonds, comprising: a solid support matrix particles (which may mean "pieces" or "strips" or the like) comprising at least 75, 80, 85, 90, 91, 92, 92.5, 93, 94, 95, 96, 97, 97.5, 98, 99, 99.1, 99.5, or 99.9 wt. % of α-cellulose, hemicellulose, and lignin, based on total support weight; and a catalytic metal comprising palladium disposed on the solid support matrix, wherein the palladium is present in an amount of from 0.01 to 1 wt. %, e.g., at least 0.01, 0.025, 0.05, 0.075, 0.1, 0.125, 0.25, 0.33, 0.375, 0.4, 0.45, or 0.5 wt. % and/or up to 1, 0.95, 0.925, 0.9, 0.875, 0.85, 0.8, 0.75, 0.67, 0.6, 0.55, or 0.5 wt. %, relative to a total catalyst weight, and wherein the solid support matrix particles have an average longest dimension of at least 1, 2.5, 5, 10, 15, 25, 33, 50, 75, 100, 125, 150, 200, 250, 300, 400, 500, 750, 1000, 1500, 2000, 2500, 3333, 5000, or 7500 µm.

The solid support matrix particles may have no average dimension less than 50, 100, 250, 300, 350, 400, 500, or 1000 µm. The α-cellulose, hemicellulose, and lignin, may be from jute stems, i.e., the support may be at least 50, 60, 70, 75, 80, 85, 90, 95, 97.5, 99, or 99.5 wt. % (or entirely) made from jute stem or a portion of the jute plant, typically comprising at least 5, 10, 15, or 20 wt. % lignin. The solid support matrix particles may comprise 20 to 60 wt. % α-cellulose, e.g., at least 20, 22, 24, 26, 28, 30, 32, 34, 36, 38, or 40 wt. % and/or up to 60, 58, 56, 54, 52, 50, 48, 46, 44, 42, or 40 wt. %, based on the total support weight. The solid support matrix particles may comprise 10 to 35 wt. % lignin, e.g., e.g., at least 10, 12.5, 15, 17.5, 20, 21, 22, 22.5, 23, 23.5, 24, 24.5, or 25 wt. % and/or up to 35, 32.5, 30, 29, 28, 27.5, 27, 26.5, 26, 25.5, 25, 24.5, 24, 23.5, 23, 22.5, 22, 21.5, 21, 20.5, or 20 wt. %, based on the total support weight. The solid support matrix particles may comprise 10 to 30 wt. % hemicellulose, e.g., 10, 12, 14, 16, 17.5, 18, 19, 20, 20.5, 21, 21.5, 22, 22.5, 23, 23.5, 24, 24.5, or 25 wt. % and/or up to 30, 28, 27.5, 27, 26.5, 26, 25.5, 25, 24.5, 24, 23.5, 23, 22.5, 22, 21.5, 21, 20.5, or 20 wt. %, based on the total support weight. The solid support matrix particles may comprise 30 to 50 wt. % α-cellulose (or any percentage or range described above, and/or at least 10, 12.5, 15, 17.5, 20, 22.5, 25, 27.5, 30, 32.5, or 35 wt. %), 15 to 30 wt. % lignin (or any percentage or range described above, and/or at least 2.5, 5, 7.5, 10, 12.5, 15, 17.5, or 20 wt. %), and 15 to 25 wt. % hemicellulose (or any percentage or range described above, and/or at least 2.5, 5, 7.5, 10, 12.5, 15, 17.5, or 20 wt. %), based on the total support weight. The support matrix particles may comprise, e.g., at least 90, 91, 92, 92.5, 93, 94, 95, 96, 97, 97.5, 98, 99, 99.1, 99.5, or 99.9 wt. % jute stems, based on the total support matrix weight.

The palladium may be in the form of nanospheres and/or have an average particle size of from 2.5 to 45 nm or 5 to 15 nm. The catalyst may comprise at least, e.g., 80, 85, 90, 91, 92, 92.5, 93, 94, 95, 96, 97, 97.5, 98, 99, 99.1, 99.5, 99.9, 99.95, or 99.99 wt. % of the palladium, relative to total metal weight in the catalyst. At least, e.g., 80, 85, 90, 91, 92, 92.5, 93, 94, 95, 96, 97, 97.5, 98, 99, 99.1, 99.5, 99.9, 99.95, or 99.99 at. % of the palladium may in elemental state.

Aspects of the invention provide methods of preparing solid-supported palladium catalysts, which methods may comprise: mixing a particulate matrix, comprising α-cellulose, hemicellulose, and lignin (in any content percentage described herein), with a palladium compound in a preferably aqueous (i.e., water containing) solution to form a suspension; combining the suspension with a reducing agent to form a mixture; and/or heating the mixture to thereby reduce at least, e.g., 50, 60, 70, 75, 80, 85, 90, 91, 92, 92.5, 93, 94, 95, 96, 97, 97.5, 98, 99, 99.1, 99.5, or 99.9 wt. % of the palladium ions, relative to total catalytic metal weight, and form the solid-supported palladium catalyst, wherein the particulate matrix comprises particles have no average dimension less than 10 µm (or any endpoint described above). While water is a desirable solvent in many applications, and may make out, e.g., 10, 15, 20, 25, 33, 40, 50, 60, 70, 75, 80, 85, 90, 91, 92, 92.5, 93, 94, 95, 96, 97, 97.5, 98, 99, 99.1, 99.5, or 99.9 wt. % of the solvent, further relevant solvents may be any in which the reaction can technically occur, e.g., pyridine, N,N-dimethylformamide (DMF), N,N-dimethylacetamide, N-methyl pyrrolidone (NMP), hexamethylphosphoramide (HMPA), dimethyl sulfoxide (DMSO), acetonitrile, tetrahydrofuran (THF), 1,4-dioxane, dichloromethane, chloroform, carbon tetrachloride, dichloroethane, acetone, ethyl acetate, pet ether, pentane, hexane(s), cyclohexane, decane(s), decalin, THF, dioxane, benzene, toluene, xylene(s), o-dichlorobenzene, diethyl ether, methyl t-butyl ether, diisopropyl ether, ethylene glycol, methanol, ethanol, isopropanol, propanol, n-butanol, and/or water. Any of these potential solvents may be combined in an aforementioned percentage to the mixed solvent, preferably miscible.

The reducing agent may comprise a phosphinic acid, a phosphinate, a phosphite, a hydride of silicon, a hydride of tin, a borohydride, diborane, a cyanoborohydride, an aluminum hydride, SMEAH, e.g., a sodium, lithium, potassium, magnesium, and/or calcium salt thereof. The reducing agent may comprise a borohydride, such as $NaBH_4$. The palladium compound may comprise palladium ion comprises a $[PdCl_4]^{2-}$ anion, such as $K_2PdCl_4$, though Useful palladium and/or platinum salts for making the inventive catalysts may include Na, K, Mg, Li, and/or $NH_4$ salts of tetrachloropalladate(II), hexachloropalladate(IV), tetracyanopalladate(II), etc., such as $K_2PdCl_4$, $K_2PdCl_6$, $K_2PtCl_4$, $K_2PtCl_6$, $Na_2PdCl_4$, $Na_2PdCl_6$, $Na_2PtCl_4$, $Na_2PtCl_6$, $Li_2PdCl_4$, $Li_2PdCl_6$, $Li_2PtCl_4$, $Li_2PtCl_6$, $(NH_4)_2PdCl_4$, $(NH_4)_2PdCl_6$, $(NH_4)_2PtCl_4$, $(NH_4)_2PtCl_6$, $K_2Pd(CN)_4$, $K_2Pd(CN)_6$, $K_2Pt(CN)_4$, $K_2Pt(CN)_6$, etc. Further useful salts may contain one or more of nitrate, chloride, bromide, iodide, acetate, formate, propionate, trifluoroacetate, tetrafluoroborate, triflate, methanesulfonate, benzenesulfonate, tosylate, sulfate, cyanide, etc., such as (ethylenediamine)palladium(II) chloride, palladium(II) bromide, palladium(II) chloride, palladium(II) cyanide, palladium(II) iodide, palladium(II) nitrate, palladium(II) sulfate, tetraamminepalladium(II) bromide, tetraamminepalladium(II) chloride, etc.

The heating may comprise treating the mixture at a temperature in a range of from 40 to 100° C., e.g., 40, 42.5, 45, 47.5, 50, 52.5, 55, 57.5, 60, 62.5, 65, 67.5, 70, 72.5, 75, 77.5, or 80° C. and/or up to 100, 95 90, 87.5, 85, 82.5, 80, 77.5, 75, 72.5, 70, 67.5, 65, 62.5, or 60° C. The heating may be conducted for a duration in the range of from 10 to 60 minutes, e.g., at least 10, 15, 20, 25, 30, 35, or 40 minutes and/or up to 60, 55, 50, 45, 40, 35, or 30 minutes.

Aspects of the invention provide processes of catalyzing a cross-coupling reaction, which processes may comprise: reacting an aryl halide (detailed below) with an optionally substituted aryl boronic acid (detailed below), or an optionally substituted alkene (detailed below) in the presence of any permutation of the inventive catalyst described herein, and a base, such as a salt comprising Li, Na, K, Mg, Cs, and/or Sr and hydroxide, carbonate, and/or bicarbonate, ammonia, ammonium hydroxide, tetramethylammonium hydroxide, tetrabutylammonium hydroxide, choline, pyridine, piperidine, piperazine, triethylamine, benzylamine, diethylamine, N-methyl piperadine, DABCO, etc., or combinations of two or more of any of these, and/or a solvent (detailed above).

The cross-coupling reaction may be a Suzuki-Miyaura reaction. The base may be potassium hydroxide and/or the solvent may comprise water. The cross-coupling reaction may be a Mizoroki-Heck reaction. The base may be potassium hydroxide, or any other described above. The solvent may comprise water and dimethylformamide in any ratio suitable.

A typical Suzuki-Miyaura reaction may take the form provided below

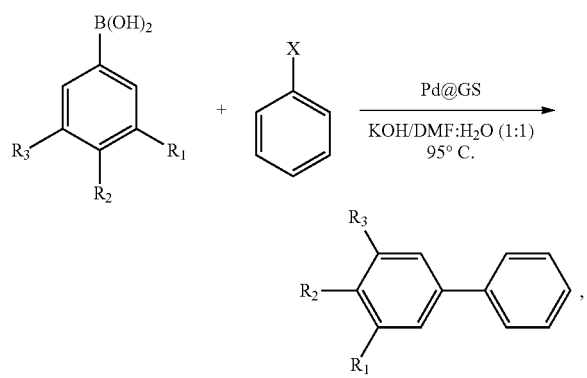

wherein $R_1$, $R_2$, and $R_3$ are independently H, methyl, ethyl, propyl, isopropyl, cyclopropyl, TMS, C4-alkyl, C5-alkyl, C6-alkyl, fluoro, nitrile, —OCH$_3$, —OCH$_2$CH$_3$, or chloro, while X may be F, Cl, Br, or I, and the halobenzene may be further substituted by any of the aforementioned, e.g., alkyl groups. While benzene rings are depicted, one or both of the rings may be naphthylene, biphenyl, anthracene, indene, indole, isoindole, phenanthrene, furan, thiophene, pyrrole, quinoline, isoquinoline, acridine, quinoxaline, quinazoline, benzofuran, isobenzofuran, benzothiophene, benzo[c]thiophene, or the like. The solvent, base, and temperatures may be modified in any way described herein.

A typical Mizoroki-Heck reaction may take the form provided below

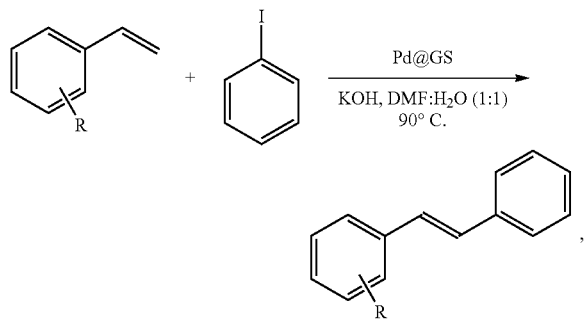

wherein R may be any of the groups identified above, the iodobenzene may be supplemented or exchanged with any of the halobenzenes (or other optionally substituted aromatics described above). The solvent, base, and temperatures may be modified in any way described herein.

Inventive catalysts may avoid silica, titania, ceria, zirconia, pseudo-boehmite, boehmite, and/or alumina, or may comprise no more than 40, 33, 25, 20, 15, 10, 7.5, 5, 4, 3, 2, 1, 0.5, or 0.1 wt. %, relative to the total support weight, of silica, titania, ceria, zirconia, pseudo-boehmite, boehmite, and/or alumina, individually or in combination. Inventive catalysts may comprise supports containing no more than 15, 10, 7.5, 5, 4, 3, 2.5, 2, 1, 0.5, 0.1, 0.01, 0.001, 0.0001, or 0.00001 at. % of N and/or S, relative to the total C—N—H—O—S content in the support, individually or in combination.

Aspects of the invention provide nanoparticle-loaded substrates that are cost effective, easy to prepare, reactive, selective, reusable, and/or environmentally friendly, optionally using naturally occurring cellulosic support with metal nanoparticles. Aspects of the invention comprise using palladium on "green support" (GS), abbreviated occasionally herein as Pd@GS or Pd-GS as "dip-catalysts," particularly with reactivity towards a series of C—C bond formation reactions, even in water.

The average size (longest dimension, diameter, length, width, and/or height) of the support particles/materials may be, for example, at least 125, 250, 375, 500, or 750 nm, or 1, 2.5, 5, 7.5, 10, 25, 50, 75, 100, 250, 500, or 750 µm. Inventive compositions may avoid dispersants, such as carboxymethyl cellulose, xylan, glucomannan, cationic etherified starch, and/or polyethylene oxide, or may comprise no more than 15, 10, 7.5, 5, 4, 3, 2.5, 2, 1, 0.5, 0.1, 0.01, 0.001, 0.0001, or 0.00001 wt. %, relative to the total catalyst weight, of such dispersants, individually or in combination. Inventive catalyst compositions may avoid cross-linking formulations including e.g., polyethyleneimine, polyacrylamide, polyvinyl alcohol, polyamide, polyols (optionally polymerized), polyisocyanates (optionally polymerized), and/or epichlorohydrin, or may comprise no more than 15, 10, 7.5, 5, 4, 3, 2.5, 2, 1, 0.5, 0.1, 0.01, 0.001, 0.0001, or 0.00001 wt. %, relative to the total catalyst weight, of such cross-linking components, individually or in combination. Inventive catalysts may avoid or substantially limit nitrogen weight in the catalyst, or may comprise no more than 1, 0.9, 0.8, 0.75, 0.67, 0.6 0.5, 0.25, 0.15, 0.1, 0.01, 0.001, 0.0001, or 0.00001 wt. %, relative to the total catalyst weight, of nitrogen mass, individually or in combination.

Inventive catalysts may avoid inorganic support materials, including zeolites, nitrogen-modified zeolites, activated carbon, silica, zirconia, alumina, titania, and/or ceria, or may comprise no more than 15, 10, 7.5, 5, 4, 3, 2.5, 2, 1, 0.9, 0.8, 0.75, 0.67, 0.6 0.5, 0.25, 0.15, 0.1, 0.01, 0.001, 0.0001, or 0.00001 wt. %, relative to the total catalyst support weight, of such inorganic(s), individually or in combination. Inventive catalyst compositions may avoid modified celluloses and/or lignins including, e.g., anionically modified (such as sulfonic acid, sulfate, phosphate, phosphonate, phosphite, etc., modified), cationically modified (such as ammonium, pyridinium, etc., modified), alkyl etherized, etc., or may comprise no more than 15, 10, 7.5, 5, 4, 3, 2.5, 2, 1, 0.5, 0.1, 0.01, 0.001, 0.0001, or 0.00001 wt. %, relative to the total catalyst weight, of such modified celluloses and/or lignins, individually or in combination. Inventive catalysts need not comprise any unnatural porphyrin compounds, salen-porphyrins, tetrapyrrole compounds, and/or pyrrole-containing compounds (e.g., macrocycles), or may contain no more than 40, 33, 25, 20, 15, 10, 7.5, 5, 4, 3, 2.5, 2, 1, 0.5, 0.1, 0.01, 0.001, 0.0001, or 0.00001 wt. %, relative to total support weight, of such unnatural porphyrin compounds, salen-porphyrins, tetrapyrrole compounds, and/or pyrrole-containing compounds, individually or in combination.

Aspects of the invention include Suzuki-Miyaura cross-coupling reactions with conversions of, e.g., at least 75, 85, 87.5, 90, 92.5, 95, 96, 97, 97.5, 98, 98.5, 99, or 99.5% with TOFs around 4692 h$^{-1}$, e.g., at least 2000, 2500, 3000, 3500, 4000, 4250, 4500, 4550, 4600, 4650, 4675, 4700, 4750, 4800, 4850, 4900, 4950, or 5000 h$^{-1}$ and/or up to 8500, 8000, 7500, 7000, 6500, 6250, 6000, 5900, 5800, 5750, or 5500 h$^{-1}$, which may be accomplished using, e.g., 4-acylphenylboronic acid and iodobenzene in the presence of KOH (or NaOH, LiOH, DABCO, Na$_2$CO$_3$, Li$_2$CO$_3$, and/or K$_2$CO$_3$) in at least 75, 80, 85, 90, 91, 92, 92.5, 93, 94, 95, 96, 97, 97.5, 98, 99, 99.1, 99.5, 99.9, 99.95, 99.99, or 99.999 wt. % water, relative to the total solvent weight. Aspects of the invention comprise Mizoroki-Heck reactions cross-coupling reactions with conversions of, e.g., at least 80, 85, 87.5, 90, 92.5, 95, 96, 97, 97.5, 98, 98.5, 99, 99.5, or 99.9% yield and with TOFs around 237 h$^{-1}$, e.g., at least 150, 175, 200, 225, 235, 240, 245, 250, 260, 267, 275, 285, 300, 325, or 350 h$^{-1}$ and/or up to 500, 450, 400, 375, 350, 325, 315, 300, 295, 290, 285, 280, or 275 h$^{-1}$, of coupling product obtained with 90, 92.5, 95, 97.5, 98, 98.5, 99, 99.5, 99.9%, or exclusive selectivity towards the targeted olefinic product, e.g., using 4-methylstyrene and iodobenzene as reactants in water-DMF as a mixed solvent (any range including, e.g., 5:1, 4.5:1, 4:1, 3.5:1, 3:1, 2.75:1, 2.5:1, 2.25:1, 2:1, 1.875:1, 1.75:1, 1.625:1, 1.5:1, 1.375:1, 1.25:1, 1.125:1, 1:1, 1:1.25, 1:1.375, 1:1.5, 1:1.625, 1:1.75, 1:1.875, 1:2, 1:2.25, 1:2.5, 1:2.75, 1:3, 1:3.5, 1:4, 1:4.5, or 1:5) at 85, 87.5, 90, 92.5, or 95° C. Inventive catalysts may be used for 5, 6, 7, 8, 9, 10, or more consecutive cycles, i.e., without addition of any fresh catalyst and/or retaining, e.g., at least 75, 80, 85, 90, 91, 92, 92.5, 93, 94, 95, 96, 97, 97.5, 98, 99, 99.1, 99.5, or 99.9% of the original crystallinity and/or original catalytic metal content, i.e., no sign of leaching was observed.

EXAMPLES

MATERIALS: All chemicals were purchased from Sigma-Aldrich and were used as received unless otherwise stated. Standard procedures were followed for drying and deoxygenating solvents. Schlenk line techniques were used to carry out reactions under an inert atmosphere wherever needed. Deionized (DI) water with a specific conductivity of 18.2 mΩ was used in all of the experiments. Fourier-transform infrared (FTIR) spectroscopic data were obtained on a Nicolet 720 instrument in the wavenumber range 400 to 4000 cm$^{-1}$, using KBr as the IR-transparent window material. Transmission electron microscope (TEM) samples were prepared by placing droplets of an ethanolic suspension of each sample on a copper grid and drying it at room temperature. The amount of Rh in the catalyst was determined by carrying out inductively coupled optical emission spectrometry (ICP-OES) using an Analytik Jena PlasmaQuant PO 9000 instrument.

The samples were first digested in a dilute mixture of HNO$_3$ and HCl. Calibration curves were prepared for Rh and Fe using ICP element standard solutions from Merck. Samples for scanning electron microscopy (SEM) were prepared from ethanolic suspensions on alumina stubs and coated with gold in an automatic Quorum Q150T E gold coater. For elemental analysis and mapping, energy dispersive x-ray spectra (EDS) were collected using a Lyra 3 attachment to the SEM. X-ray photoelectron spectroscopic (XPS) studies were carried out with XPS Microprobe from Thermo Scientific (USA), which was equipped with an ESCALAB-250Xi Al-Kα micro-focusing x-ray monochromator for the chemical analysis of the synthesized nanoparticles (NPs) on the support. Catalytic products were identified using a Shimadzu 2010 Plus (Japan) gas chromatograph attached to a mass spectrometer. The disappearance of the reactant and sequential appearance of the product were recorded in real time. The species were identified by comparing their molecular ion (M$^+$) peaks to the Wiley Registry of Mass Spectral Data, in addition to analyzing the mass fragmentation.

SYNTHESIS OF THE CATALYST: Pd decorated on the jute strips was fabricated per the procedure given below. To an aqueous solution of K$_2$PdCl$_4$ (32 mg, 0.098 mmol), a sufficiently oven-dried jute strip with dimensions of 2×0.5× 0.1 cm (0.1 cm$^3$ in volume) was inserted into a vial and allowed to soak for 2 hours. Sodium borohydride (40 mg, 1 mmol) in water (1 mL) was added to the vial containing the soaked jute strip at a temperature 80° C. The initially yellowish jute strip started to become black, and the reduction appeared complete within 20 minutes, as no more color change was observed. The vial and its contents were heated at 80° C. for another 3 hours, after which the strip was removed and dried in open air for 48 hours.

EXEMPLARY PROCEDURE FOR THE CATALYTIC SUZUKI-MIYAURA REACTION: The Suzuki-Miyaura reaction was conducted according to a procedure described in *Chem. Eur. J.* 2013, 19, 11963-11974, which is incorporated by reference herein in its entirety. The Suzuki-Miyaura reaction was carried out generally as described, but in a 10-fold reaction parallel reactor system. To a reaction vessel, iodobenzene (134 µL, 1.2 mmol), phenylboronic acid (122 mg, 1.0 mmol) and potassium hydroxide (84 mg, 1.5 mmol) in 10 mL of water were added, and the reaction mixture was stirred for 15 minutes. A catalyst strip with dimensions of 2 cm×0.5 cm×0.1 cm was inserted and refluxed in the reaction mixture. The samples were withdrawn periodically and analyzed using thin layer chromatography (TLC) to monitor the progress of the reaction. The product was extracted from the aqueous reaction mixture using ethyl acetate. The concentrated residue was passed through a short silica gel column, followed by elution with a 9:1 mixture of hexane: ethyl acetate, then injection into a gas chromatograph (GC) to determine the percent conversion values.

TYPICAL PROCEDURE FOR THE CATALYTIC MIZOROKI-HECK REACTION: The Mizoroki-Heck conducted according to a procedure described in *Chem. Eur. J.* 2013, 19, 14425-14431, which is incorporated by reference herein in its entirety. The Suzuki-Miyaura reaction was carried out generally as described, in air and in a parallel reactor equipped with a 10-fold reaction parallel reactor system. A reaction vessel containing a magnetic stir bar was charged with styrene (1.0 mmol, 0.12 mL), iodobenzene (134 µL, 1.2 mmol) and potassium hydroxide (1.0 mmol, 56 mg) dispersed in 10 mL of DMF:water (1:1) for 10 minutes. The palladium on green support (jute stem) catalyst, i.e., "Pd@GS," strip with dimensions of ~2 cm×0.5 cm×0.1 cm, was introduced into the styrene, iodobenzene, KOH, and catalyst reaction system, and the temperature was maintained at 90° C. for the duration of the subsequent reaction. The progress of the reaction was monitored using TLC and the product was extracted using ethyl acetate, passed through a short silica gel column, followed by elution with hexane:ethyl acetate (9:1), and then injection into a gas chromatograph (GC) to determine the percent conversion values.

Aspects of the invention include dip-catalysts, particularly based on Pd nanoparticles on a green support, which may be useful for realizing C—C bond formation reactions, even in water. Aspects of the invention include Suzuki-Miyaura C—C bond formation reactions, e.g., with a variety of optionally substituted phenylboronic acids, using inventive catalysts, including with selectivity. Aspects of the invention provide catalytic compositions which are suitable to catalyze Mizoroki-Heck coupling reactions, with up to quantitative conversion, generally in short spans of time. Aspects of the invention comprise robust catalytic systems, e.g., reusable for at least 5, 6, 7, 8, 9, 10, 11, 12, 13, 14, or 15 cycles for Suzuki-Miyaura cross-coupling reactions, even in water or in the presence of water, with at least 75, 80, 85, 90, 91, 92, 92.5, 93, 94, 95, 96, 97, 97.5, 98, 99, 99.1, 99.5, or 99.9% of the TOF, catalytic metal content, and/or selectivity of the initial reaction. Aspects of the invention comprise environmentally benign catalysts and their fabrication, alongside unexpectedly superior catalytic coupling reaction activity (relative to predictions or known alternatives) for a series of olefins and halobenzenes, which may offer new routes to develop catalysts with other metal nanoparticles for various catalytic transformations.

Referring now to the drawings, wherein like reference numerals designate identical or corresponding parts throughout the several views.

FIG. 1 depicts an exemplary procedure useful for synthesizing exemplary inventive catalytic constructs including palladium on jute stems, i.e., Pd@GS strips. In the first step, a retting process was used to extract jute sticks from the jute plant. These jute sticks were cut into pieces having dimensions of 2×0.5×0.1 cm and oven dried at 100° C. overnight. The oven-dried strips were allowed to soak in a solution of $K_2PdCl_4$ for 2 hours, then reduced with a sodium borohydride suspension in water at temperature of 80° C. The sticks immediately turned black after the addition of $NaBH_4$, indicating that $PdCl_4$ ions entrapped by the cellulosic support were reduced to elemental Pd nanoparticles.

Figure 2A:
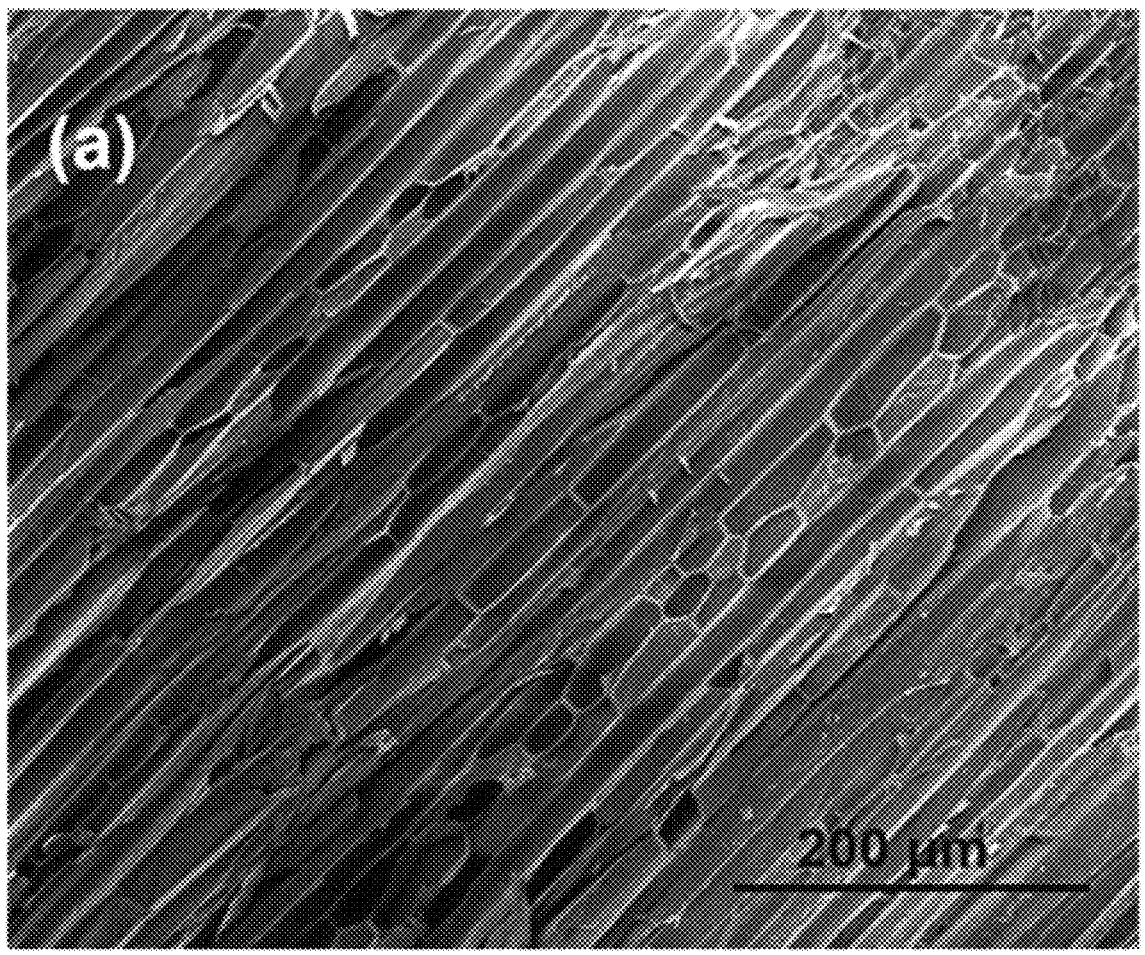
FIG. 2A shows a scanning electron microscope (SEM) image of an exemplary pure jute strip useful as a support.
Figure 2B:
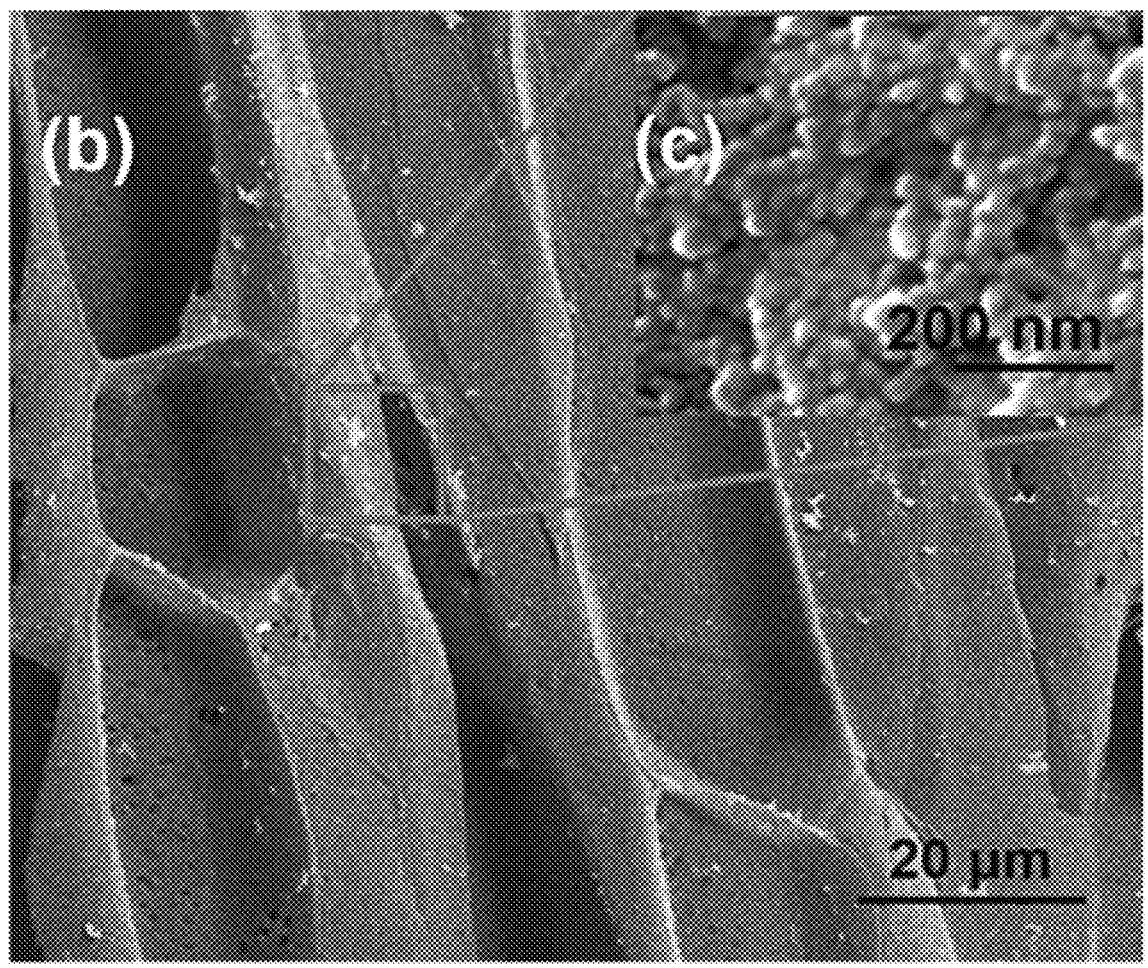
FIG. 2B shows an SEM image of an exemplary Pd@GS strip including a 100-fold scale-up inset in the upper right of the Pd nanoparticles on the pure jute stem.
Figure 2C:
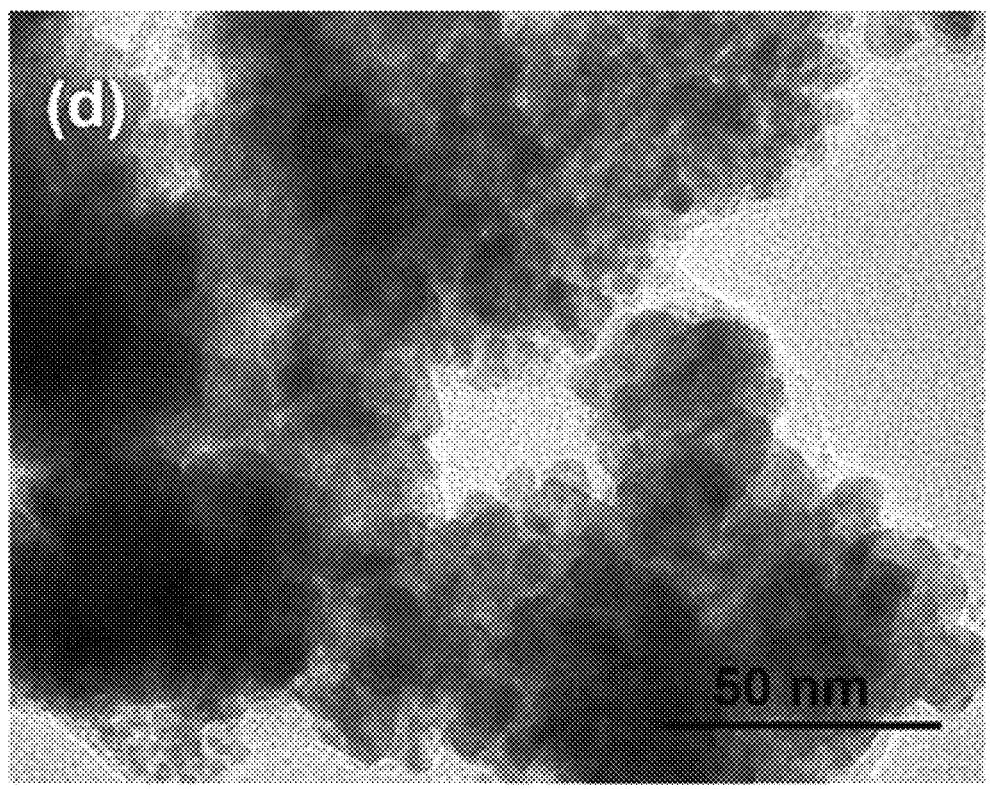
FIG. 2C shows a transmission electron microscope (TEM) image of an exemplary Pd@GS catalyst material on a 50 nm scale, showing the Pd nanoparticles.
Figure 2D:
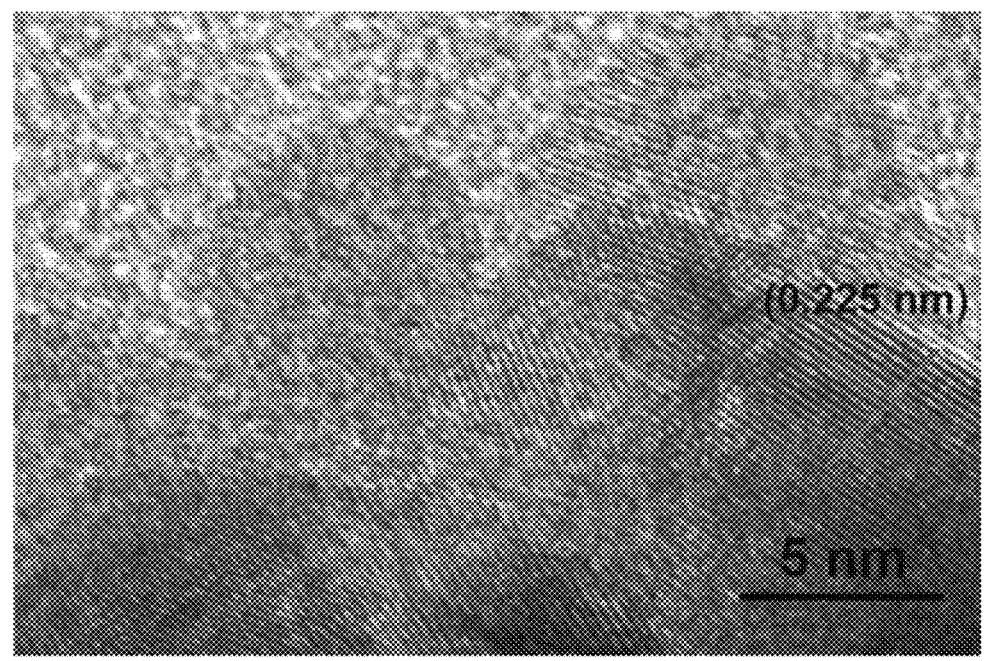
FIG. 2D shows a high resolution transmission electron microscope (HRTEM) image of an exemplary Pd@GS catalyst material on a 5 nm scale.

FIG. 2A to 2D show field emission-scanning electron microscope (FE-SEM) and transmission electron microscope (TEM) images of pure (FIG. 2A) and decorated jute sticks (FIG. 2B to 2D). Inspection of the images, particularly the embedded portion "(c)" in FIG. 2B, indicate that spherical Pd nanoparticles formed, with average dimensions of 7 to 10 nm, which may include an average longest dimension (or diameter) of, e.g., at least 5, 5.5, 6, 6.5, 7, 7.5, 8, 8.5, 9, 9.5, 10, 12.5, or 15 nm and/or no more than 20, 17.5, 15, 12.5, 12, 11.5, 11, 10.5, 10, 9.5, 9, 8.5, 8, or 7.5 nm. The pure jute support may have a pattern of substantially parallel ribs with average lengths of, e.g., at least 500, 750, 1000, 1250, 1500, 2000, 2500, 3000, or 5000 µm and/or up to 5, 4, 3.5, 3, 2.5, 2.25, 2, 1.75, 1.5, 1.25, or 1 mm, rib thicknesses of, e.g., 0.01, 0.025, 0.05, 0.075, 0.1, 0.25, 0.5, 1, 1.5, 2, 2.5, or 3 µm and/or up to 20, 17.5, 15, 12.5, 10, 9, 8, 7.5, 7, 6.5, 6, 5.5, or 5 µm, and/or inter-rib spacings of, e.g., at least 5, 7.5, 10, 12.5, 15, 17.5, or 20 µm and/or up to 50, 45, 40, 35, 30, 25, or 20 µm. At higher magnification, i.e., FIG. 2B inset labelled "(c)," the Pd nanoparticles generated according to the Example can be observed to have spherical shapes and to be highly uniform in size. The TEM image of the exemplary "dip-catalyst" in FIG. 1C reveals a uniform distribution of spherical Pd nanoparticles with dimensions of 7 to 10 nm. Inspection of an high resolution transmission electron microscope (HR-TEM) image of the "dip-catalyst" in FIG. 1D indicates the presence of typical metallic Pd nanoparticles with a lattice spacing of 0.225 nm, which can be assigned to the <111> plane of the metallic Pd.

Figure 3A:
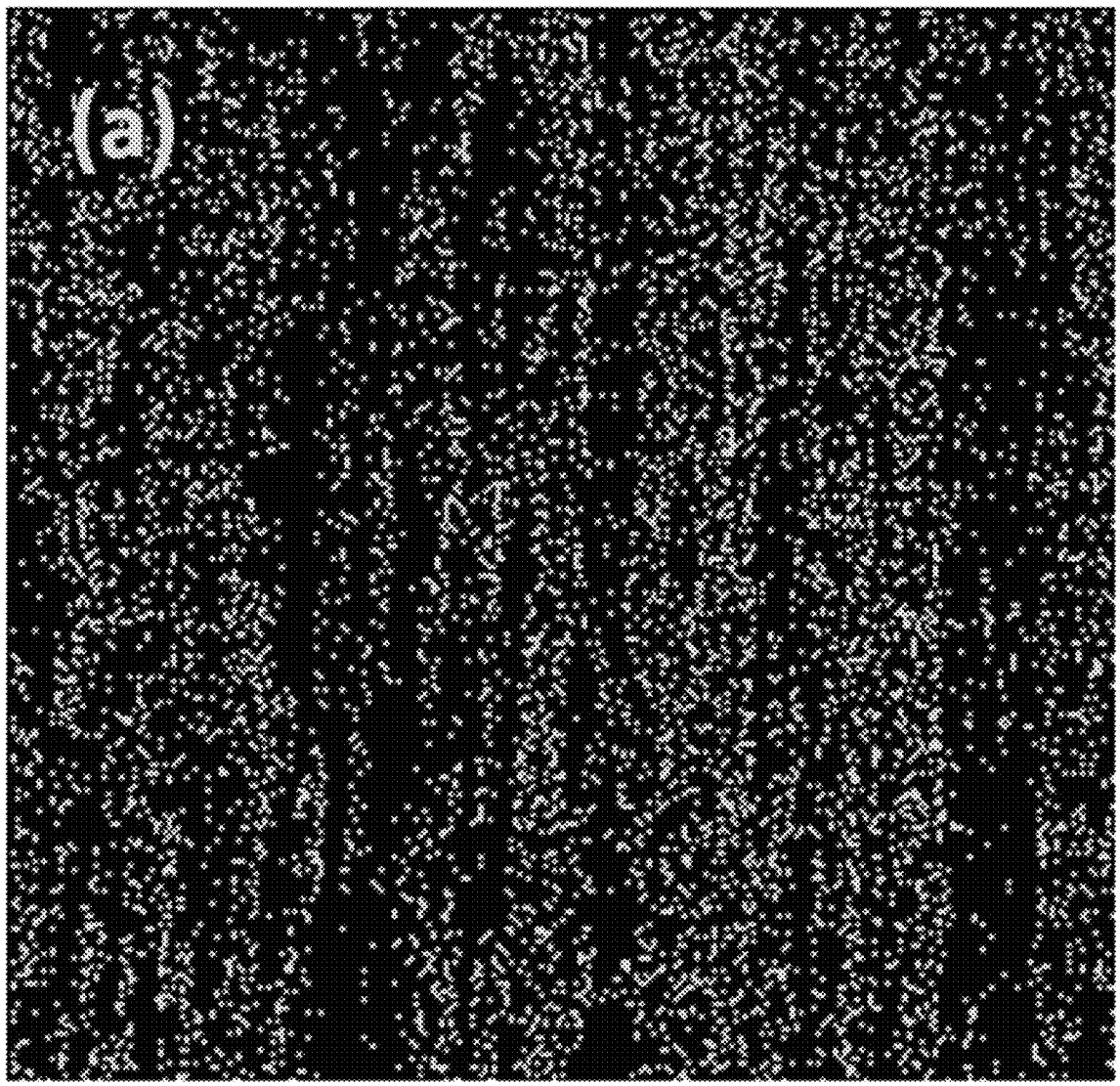
FIG. 3A shows an elemental mapping of Pd@GS for carbon.
Figure 3B:
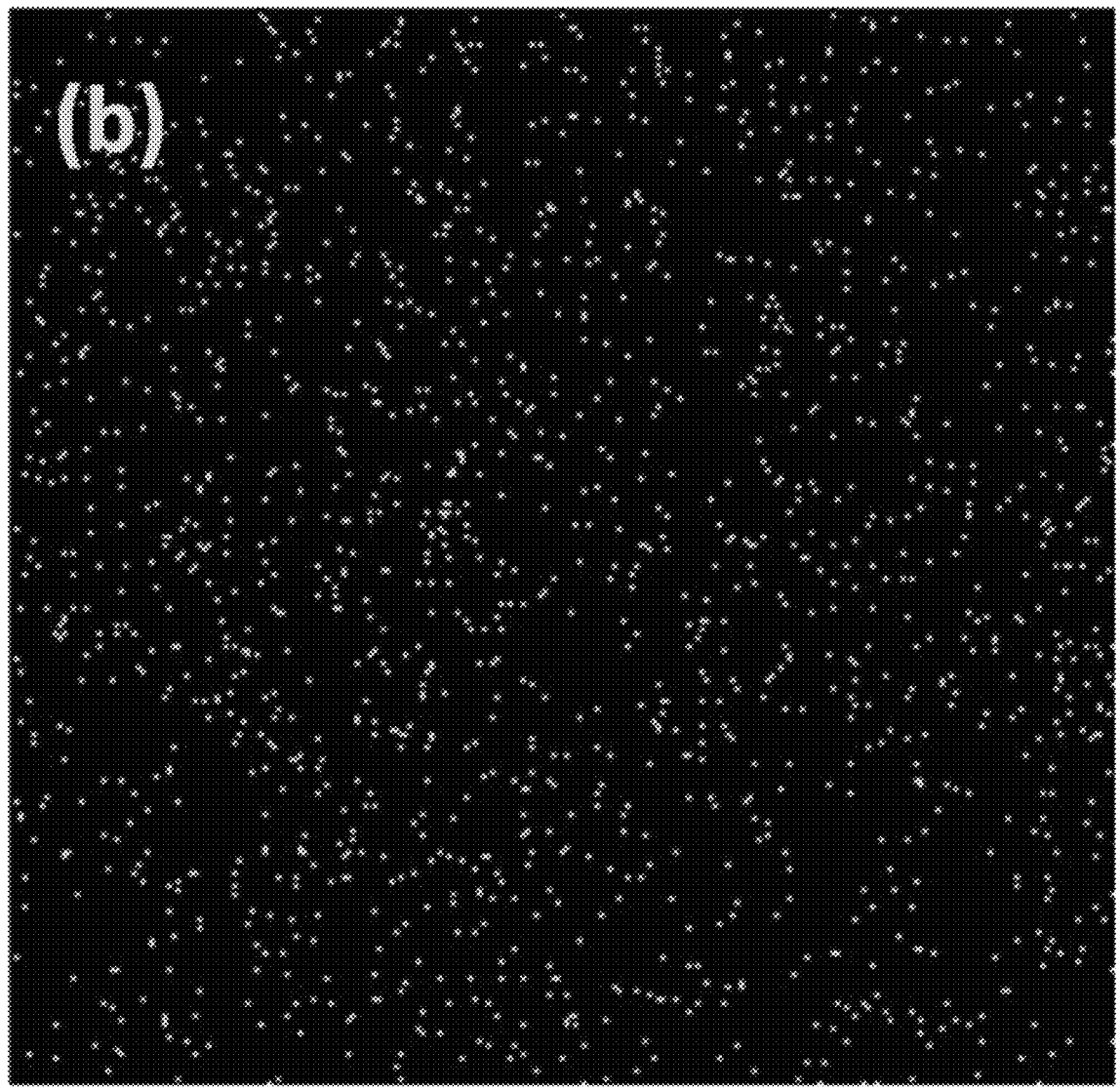
FIG. 3B shows an elemental mapping of Pd@GS for Pd nanoparticles.
Figure 3C:
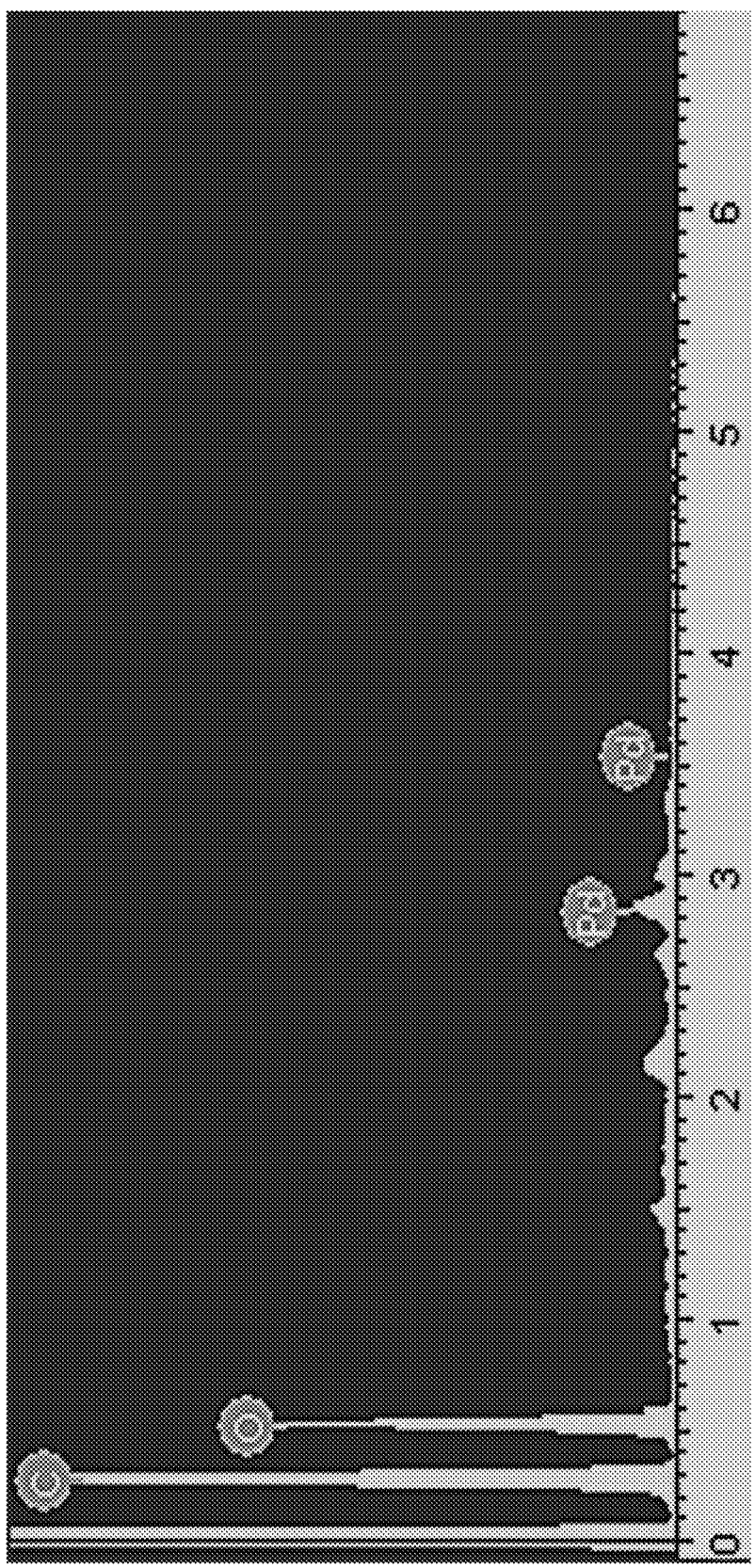
FIG. 3C shows an energy-dispersive X-ray spectroscopy (EDS, EDX, EDXS, or XEDS) of an exemplary Pd@GS catalyst material.

FIGS. 3A and 3B show elemental mappings of the whole area of a Pd@GS sample, with FIG. 3A showing C atoms, derived from cellulose, lignin, etc., as white dots, and FIG. 3B showing Pd atoms as pink dots. These mappings indicate a uniform distribution of the Pd nanoparticles throughout the strip. Energy dispersive x-ray spectroscopy (EDS) data, shown in FIG. 3C, indicates that Pd nanoparticles are present on the surfaces of the strips, in addition to the C and O atoms.

Figure 4A:
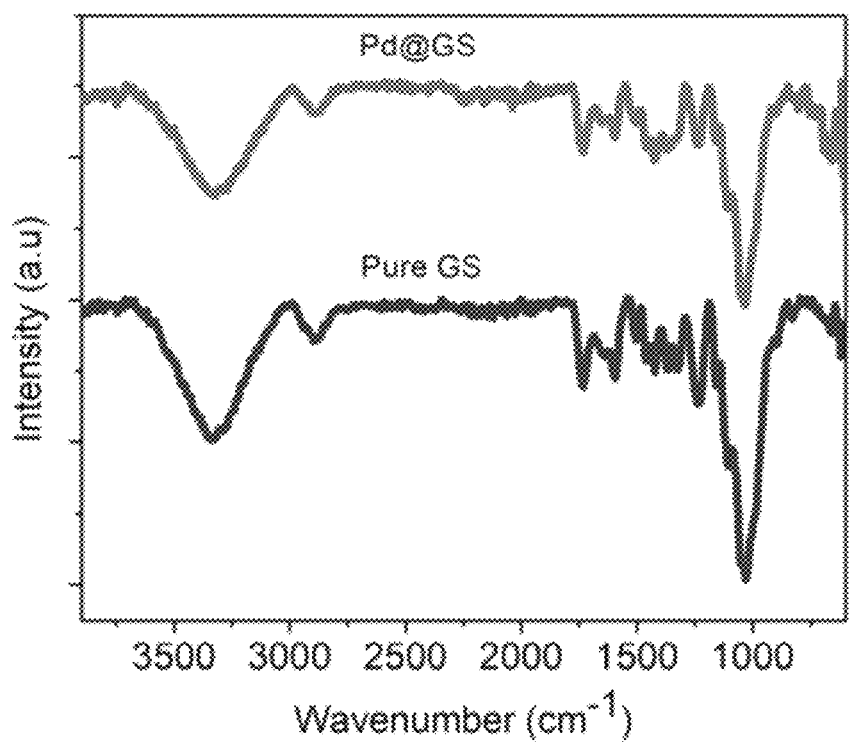
FIG. 4A shows Fourier-transform infrared (FTIR) spectra of pure jute stem (GS) support (lower spectrum) and an exemplary Pd@GS catalyst material (upper spectrum)

FIG. 4A shows Fourier-transform infrared (FTIR) spectra of pure jute strips (lower spectrum) as well decorated strips (upper spectrum) and these data. In the FT-IR spectrum of palladium on jute stick, i.e., Pd@GS, a band was observed at 2895 cm$^{-1}$ that may be assigned to an aliphatic C—H bond stretching vibration, with this aliphatic coming from the cellulosic support. A band was also observed at 1590 cm$^{-1}$, which may be attributed to the bending vibration of the C—H bond. No noticeable structural change was observed after the incorporation of Pd nanoparticles, indicating no distortion or damage to the cellulosic support even when treating it under a reducing environment.

Figure 4B:
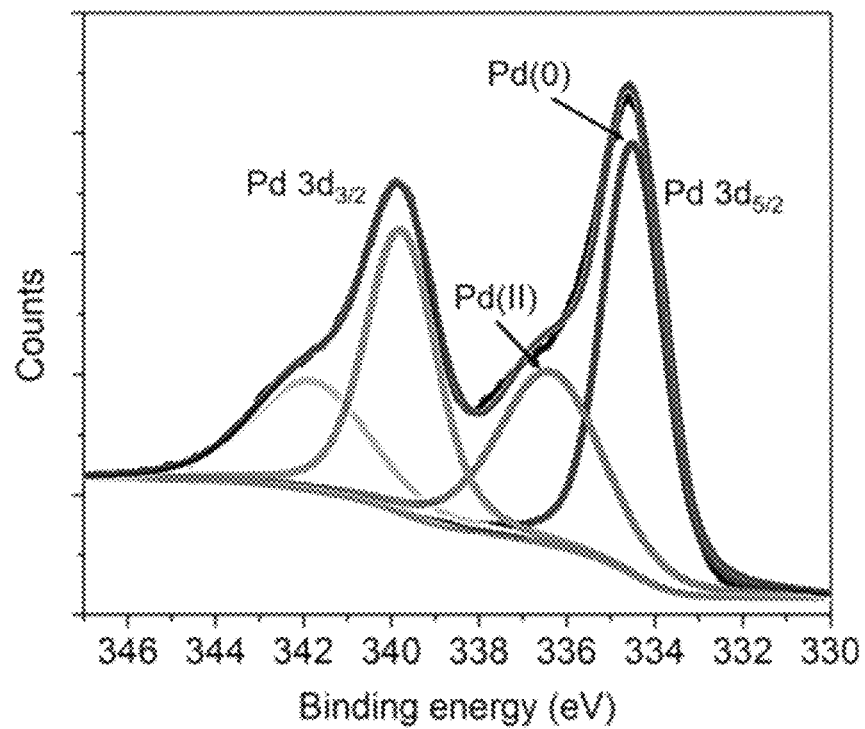
FIG. 4B shows x-ray photoelectron spectroscopy (XPS) spectra of an exemplary Pd@GS catalyst material.

FIG. 4B show x-ray photoelectron spectroscopy (XPS) results useful for examining the chemical composition and chemical states of the elements in the Pd@GS. The survey spectrum in FIG. 3C reveals that the elements C, O, and Pd are present in the exemplary catalytic material. The XPS spectrum in the Pd 3d region of FIG. 4B shows a doublet of peaks at binding energies of 335.3 and 340.6 eV, which can be assigned to Pd d5/2 and Pd 3d3/2 species arising from spin-orbital splitting in the metallic $Pd^0$. Relatively low-intensity peaks also appear at 337.3 and 342.6 eV in the spectra of FIG. 4B, corresponding to $Pd^{2+}$ species that may have resulted from the long exposure of the dip-catalyst to air. The relative amount of Pd was also determined from an inductively coupled plasma optical emission spectroscopy (ICP-OES) analysis, which specifically indicated the presence of 0.044 mg (0.413 µmol) of Pd per jute-stick strip having dimensions of 2×0.5×0.1 cm (0.1 cm$^3$), i.e., roughly 0.33 mg/cm$^3$ or 3.18 µmol/cm$^3$ for a jute density of 1.3 g/cm$^3$. The reproducibility of loading of palladium nanoparticles was investigated by varying the concentration of the Pd precursor, $K_2PdCl_4$. The loading Pd on GS was increased with the higher concentration of pre-reduced Pd and then remained constant with an average Pd content determined to be 0.044 mg per strip. Hence, the reproducibility of the Pd nanoparticles loading, using $NaBH_4$ as reducing agent, implies a natural limit to the highly hydroxylated surface of jute stick.

The catalytic activity of Pd@GS for Suzuki-Miyaura cross-coupling reactions was evaluated using the exemplary jute-stick-supported Pd nanoparticles (dip catalyst), i.e., Pd@GS, and the results are summarized in table in FIG. 5. For each reaction carried out, only one Pd@GS catalyst strip with dimensions of 2×0.5×0.1 cm, determined using inductively coupled plasma optical emission spectroscopy (ICP-OES) to contain 0.044 mg of Pd nanoparticles, was used. Initially, to optimize the reaction conditions, phenylboronic acid and iodobenzene were chosen as model substrates. The effects of various parameters, such as temperature, and the nature of solvents and bases, were investigated. Control conditions including phenylboronic acid and iodobenzene but omitting Pd@GS catalyst yielded no conversion, indicating the necessity of using a catalyst, Pd@GS.

Various bases, including $K_2CO_3$, $Na_2CO_3$, $NaHCO_3$, triethylamine (TEA), and KOH, were each tested in aqueous medium at 90° C. (FIG. 5, entries 1 to 5). KOH was found to be well suited, having produced an almost quantitative (98%) conversion with maximum selectivity (FIG. 5, entry 5) with higher turn-over frequency (TOF) value, i.e., 2298 h$^{-1}$. Lower yields resulted from using weaker bases like $Na_2CO_3$, $K_2CO_3$, and $NaHCO_3$, and the lowest yield in aqueous medium was observed when using triethylamine (TEA) in entry 4 of FIG. 5. Hence the reactivity order revealed for the bases in this reaction was KOH>$K_2CO_3$>$Na_2CO_3$>$NaHCO_3$>TEA. Analogous bases may be similarly situated, such as LiOH, NaOH, RbOH, and/or CsOH, as well as bases with similar basicity and/or $pK_a$ ($pK_b$), such as no more than 1, 0.75, 0.5, 0.25, 0.1, 0.01, 0, −0.1, −0.25, −0.5, or −0.67.

After selecting the base, various solvents were tested for their effects on the cross-coupling reaction using KOH as the base, with these solvents including water (FIG. 5, entry 5), DMF (FIG. 5, entry 6), toluene (FIG. 5, entry 7) and a 1:1 mixture of ethanol and water (FIG. 5, entry 8). The use of aprotic DMF and non-polar toluene as solvents each appeared to suppress the conversion even after an extended time period while a significant improvement in conversion was observed by employing the protic solvent, water.

The role of temperature was also tested, as seen in entries 9 to 17. On decreasing the reaction temperature from 90° C. (FIG. 5, entry 5) to 50° C. (FIG. 5, entry 9), the turn-over frequency (TOF) became lower, and the percent conversion achieved in 5 hours was 57%. Furthermore, no conversion was achieved at room temperature. Therefore, based on the above experiments with exemplary catalysts, the best conversion with exclusive selectivity was achieved at 90° C. using KOH as base in water—a most benign solvent.

After setting up the reaction conditions, the effects of the functional groups attached to the benzene ring in the boronic acid were explored, including halides of the various halobenzenes (X being I, Br, and Cl) on the C—C bond formation reaction. Of the reactions of the different halobenzenes with phenylboronic acids, iodobenzene was found to have the highest TOF value, i.e., entry 5 at 2298 $h^{-1}$, versus entry 10 at 1427 $h^{-1}$ and entry 11 at 544 $h^{-1}$, with phenylboronic acid and a higher percent conversion than the corresponding bromo and chlorobenzenes (FIG. 5, entries 5, 10, and 11).

Similar trends were found for the reactions of the different halobenzenes with both 4-acyl and 3,5-dimethyl phenylboronic acids. In the case of 4-acylphenyl boronic acid, the percent conversion achieved with iodobenzene was 97% (FIG. 5, entry 12), while the TOF achieved was 4692 $h^{-1}$. No significant electron-withdrawing or electron-donating effect on the phenyl boronic acid substrate was noticeable, as evident from comparing the reactions using 4-acylphenyl boronic acid with those using 3,5-dimethyl phenylboronic acids (FIG. 5, entries 12 to 17). In the case of bromobenzene, the conversion was higher, i.e., 89%, with 3,5-dimethylphenyl boronic acid (FIG. 5, entry 16) than with the 4-acyl phenylboronic acid at 75% (FIG. 5, entry 13). On the other hand, comparable reactivity, i.e., TOF 919 and 971 $h^{-1}$, was observed for chlorobenzene with either the acyl and dimethyl-substituted boronic acids (FIG. 5, entries 14 and 17).

The pure green support (GS), i.e., jute stem, was tested to determine whether its role was only as a support or also as a catalyst. For pure jute stem (GS), no conversion to the coupling product was found (FIG. 5, entry 18). Hence, GS was acting only as a support and solely the Pd portion of the Pd@GS was serving as the catalyst.

Standard catalysts, such as palladium dichloride ($PdCl_2$), palladium tetrakis triphenylphosphine ($Pd(PPh_3)_4$) and palladium on carbon, were also tested (FIG. 5, entries 19 to 21). The reactivity results using standard catalysts were found to be comparable to those of the exemplary inventive Pd@GS, but the reusability of the standard catalysts was more restricted. In addition, the price of jute stick, as support used in Pd@GS, is much cheaper than that of the charcoal in Pd/C.

Figure 6:
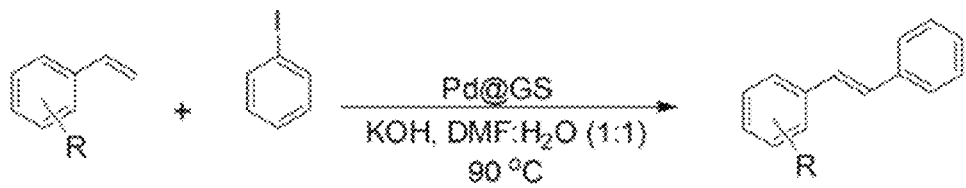
FIG. 6 shows a table presenting data on reaction conditions and efficiencies of an exemplary Pd@GS catalyst material in the catalysis of Mizoroki-Heck cross-coupling reaction in various conditions.

FIG. 6 shows tabulated results of Mizoroki-Heck cross-coupling reactions under various conditions using styrene and iodobenzene as reactants and 2 cm of Pd@GS strips as the catalyst. No conversion was achieved in the absence of catalyst.

The effect of solvent on the conversion and selectivity was studied, and since the conversions and selectivity are highly dependent on solvent, the coupling reaction was tested in various solvents and combination of solvents such as water, DMF, ethanol, water-ethanol, and water-DMF (FIG. 6, entries 1 to 7). The reaction was rather slow in pure water (FIG. 6, entry 1), ethanol (FIG. 6, entry 2), and DMF (FIG. 6, entry 4). Even after prolonging the reaction time to 24 hours using KOH as the base, the highest conversion achieved in pure water was 79% (FIG. 6, entry 1). A significant amount of the biphenyl compound was produced as a side product, which was not desired. Higher conversion percentages were observed when employing mixtures of solvents (FIG. 6, entries 3, 6, and 7). In a 1:1 mixture of ethanol and water (FIG. 6, entry 3), 82% of the iodobenzene was converted to the corresponding coupled product. The most significant improvement was obtained using a 1:1 mixture of DMF and water as the solvent, and KOH as the base, at a conversion of 97% (FIG. 6, entry 7) and higher TOF value (235 $h^{-1}$) with nearly perfect selectivity. This improvement may have been due to better solubility of the substrate and inorganic base in the mixture of DMF and water, rather than in just water.

The effect of temperature on the reaction when using a mixture of DMF and water as the solvent was also evaluated. On lowering the temperature to 50° C., the reaction slowed down and only 71% conversion was found even after 24 hours (FIG. 6, entry 6) and TOF was lowered down to 72 $h^{-1}$.

The effect of base was briefly examined. Replacing the strong base, KOH, with the mild base, $K_2CO_3$, resulted in a poorer conversion. Based on the above results taken together, the Mizoroki-Heck cross-coupling reaction using an exemplary 2 cm strip of Pd@GS as a dip catalyst was found to be excellent at 90° C. in the presence of KOH as the base in a 1:1 mixture of DMF and water as the solvent (FIG. 6, entry 7).

FIG. 6 also shows the results of an analysis of the catalytic activity and selectivity for the cross-coupling reaction on a series of styrenic compounds with varied organic functional groups at 90° C. in the presence of KOH as the base in a 1:1 mixture of DMF and water as the solvent. In the case of the 4-methylstryene, the conversion achieved was 98% (FIG. 6, entry 9) with a TOF value of 237 $h^{-1}$. Decreasing the catalyst loading by shortening the length of the strip to 1 cm length of catalyst strip, while otherwise keeping the same reaction conditions and duration resulted in a drastically lower reaction rate, and only a 69% coupling (FIG. 6, entry 10). The reaction of styrene with arylbromide proceeded to 97% conversion (FIG. 6, entry 8) in 24 hours under the same reaction condition.

The effects of various electron-withdrawing and electron-donating groups on the styrene moiety on the conversion were also investigated and the results are provided in FIG. 6. In the case of 4-vinyl anisole 96% conversion of the starting material was achieved (FIG. 6, entry 11), and with 4-chlorostyrene, 97% of the starting compound converted to product in 10 hours (FIG. 6, entry 12). Surprisingly, the conversion of 3-nitrostyrene (FIG. 6, entry 13) decreased to 88%, even after prolonging the reaction time to 24 hours. The conversion of 2-bromostryrene also required 24 hours to reach a suboptimal level of 95% (FIG. 6, entry 14). In the 2-bromostryrene reaction, <3% of a configurational isomer of coupling product was also detected in GC and identified by GC-MS.

A control reaction was carried out in the presence of a pure jute strip under similar reaction conditions, in order to establish the roles of the jute support and Pd in the Pd@GS construct. With pure jute strip (no Pd), no conversion of styrene to its corresponding coupling product was found (FIG. 6, entry 14), indicating that the catalytic activity of Pd resided in the Pd@GS. Using styrene under otherwise identically reaction conditions, standard catalysts were also tested (FIG. 6, entries 16 to 18). The standard catalysts were found to be active and the conversion in each case was quantitative but with limited reusability of the spent catalyst.

In addition to its utility in active catalysts and reusability, jute-stick has further advantages as support. Jute-stick is superior to magnetic nanoparticle supports in economic viability, ease of separation of catalyst from the reaction system, and non-toxicity. This is because jute-stick is a naturally occurring source (green), economically cheap (0.2 USD per kg in India), and reusable for multiple cycles.

FIG. 7 shows tabulated results analyzing the efficacy of the catalyst, Pd@GS, comparing data with various catalytic system reported in literature on the results of the Suzuki-Miyaura coupling reactions between iodobenzene and phenylboronic acid under similar reaction condition. From the values in the table in FIG. 7, the inventive catalysts, Pd@GS, can have considerably higher activity in the form of catalytic turn-over frequency, i.e., TOF 2298 $h^{-1}$, than reported systems in the art.

As shown in FIG. 8, a similar trend was observed in case of Mizoroki-Heck coupling reaction with arylbromides and styrene under the selected conditions. Hence, inventive catalyst systems can offer a better approach in terms of using a green support (devoid of any metal oxides as support), ease of deployment and removal of catalyst ("dip catalyst"), smart design of the catalyst construct, high thermal stability, versatility to a wide range of systems, optimum conversion and selectivity and recyclability over several runs.

Figure 9:
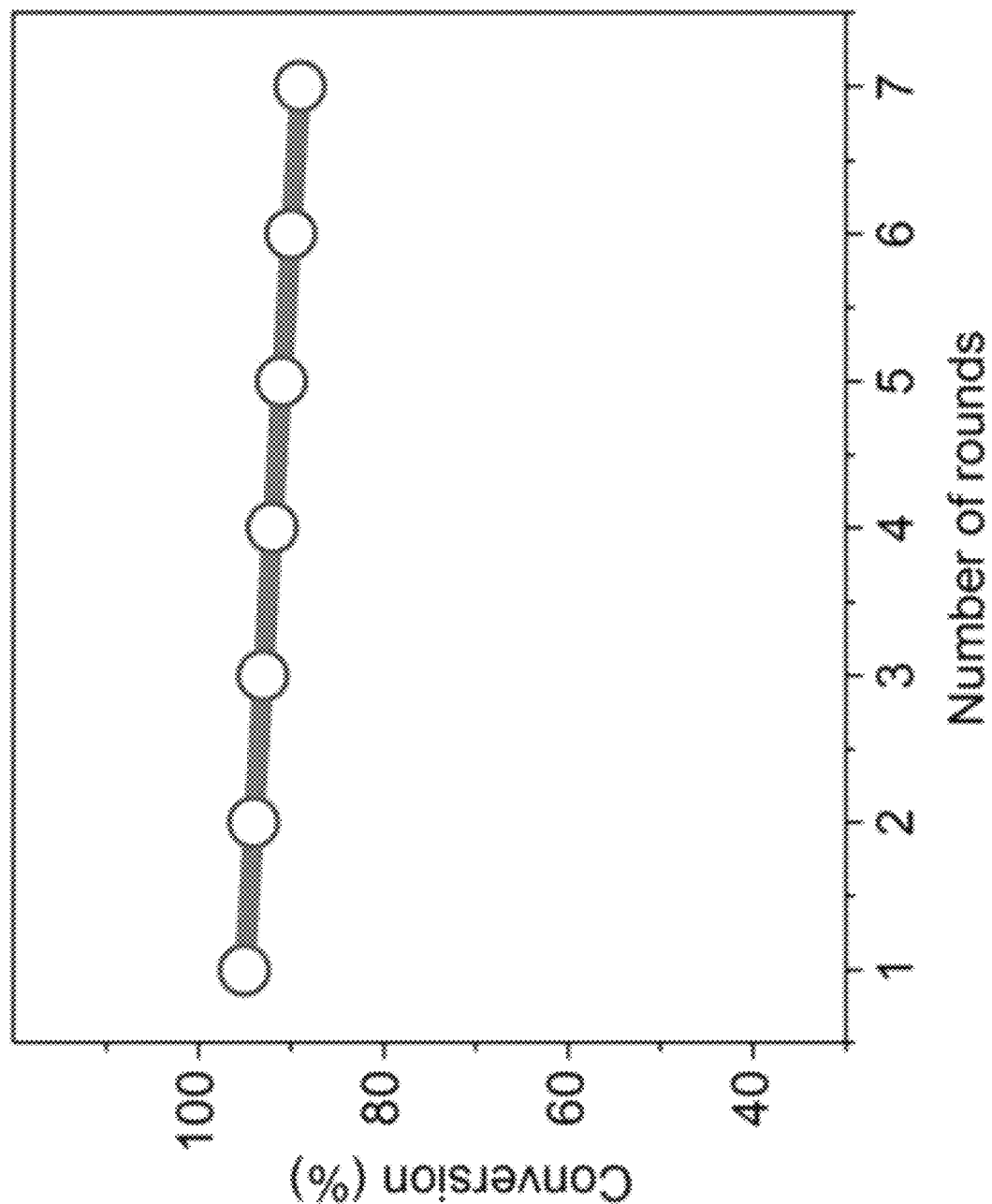
FIG. 9 shows a plot illustrating the reusability of the Pd@GS catalyst for Suzuki-Miyaura coupling reactions at 90° ° C. in water on phenylboronic acid and iodobenzene with KOH.

FIG. 9 shows the results of an investigation into the robustness and stability of the fabricated Pd@GS catalyst, reusing spent catalyst in subsequent Suzuki-Miyaura coupling reactions in aqueous medium under otherwise identical reaction conditions, i.e., 90° C. in the presence of KOH as the base in a 1:1 mixture of DMF and water as the solvent. After each cycle, the Pd@GS strip was taken out of the reaction mixture, and the residue was analyzed for conversion and selectivity, then the strip was thoroughly washed with water and ethanol and dried for next coupling reaction, all without addition of any fresh catalyst strip or metal. The reused catalyst was found to be consistently active through 6 or 7 cycles (FIG. 9), whereafter the conversion % began degrading. A leaching study was performed for the samples taken in cycles 1, 3, 5 and 7. No trace was detected in cycle 1 or 3, but a measurable amount of Pd was found in the cycle 7 which is about 8% of the total Pd decorated onto the strip. This leaching is the probable reason for the eventual loss of activity in the inventive catalyst system. The degradation may have been due to its exposure to a highly corrosive reaction environment having resulted in leaching of Pd nanoparticles from the strip.

Figure 10:
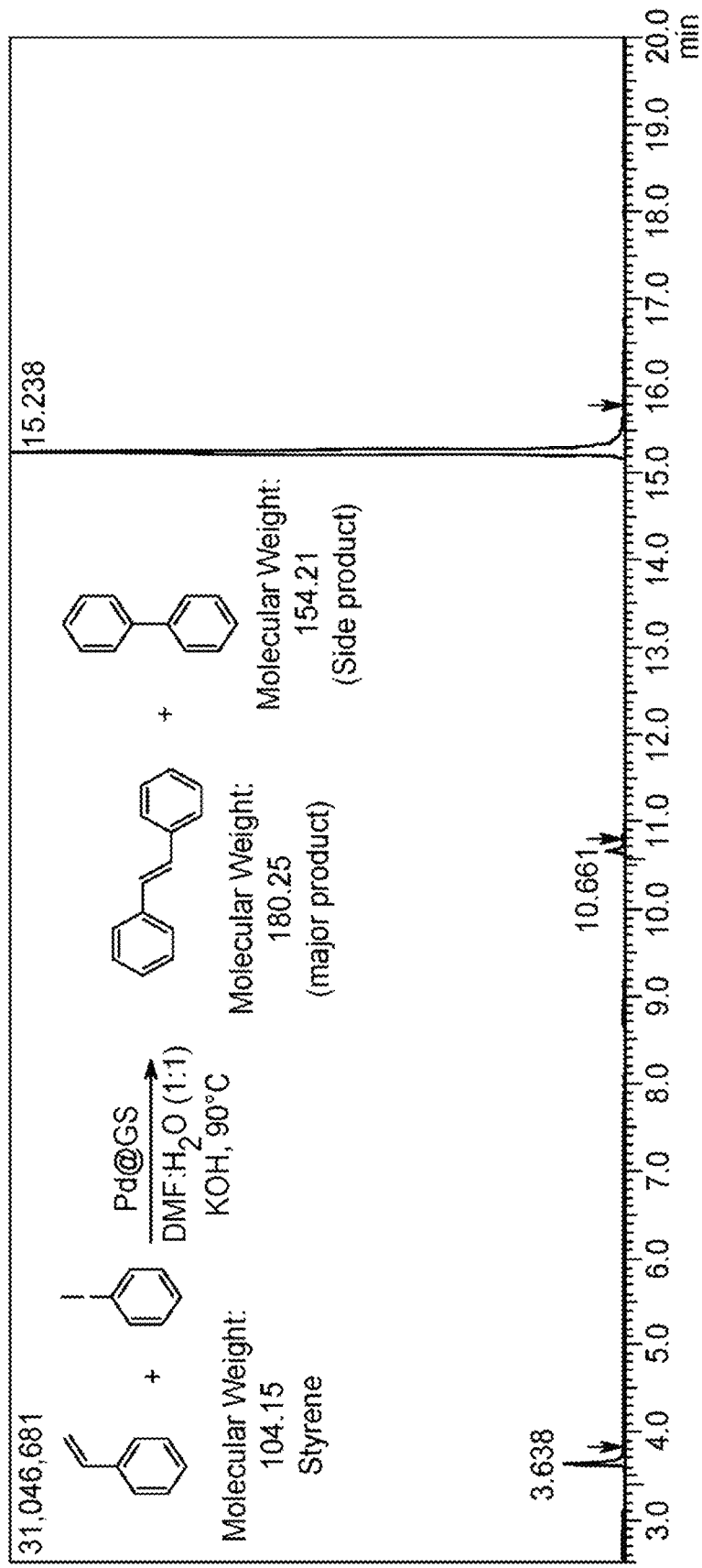
FIG. 10 shows a gas chromatography (GC) plot a the coupling reaction of styrene and iodobenzene in a Mizoroki-Heck reaction using an inventive catalyst.
Figure 11A:
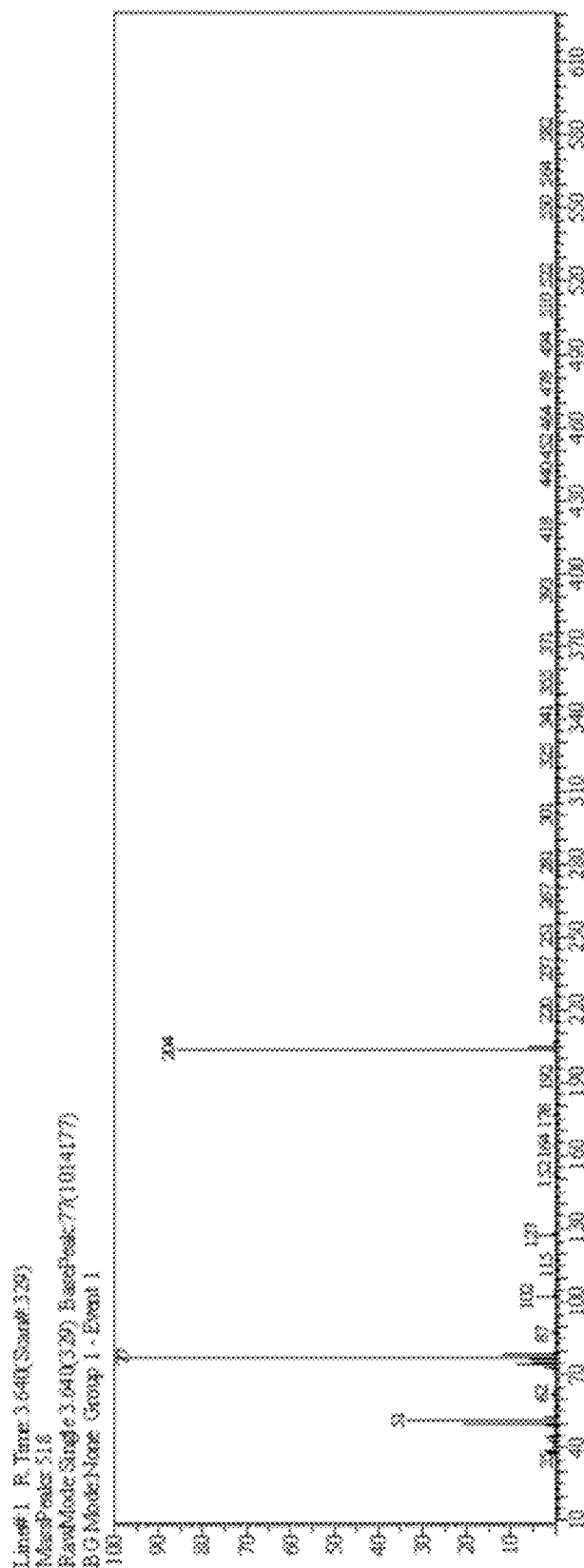
FIG. 11A shows a mass spectrum of GC peck from FIG. 10 at an R$_t$ of 3.640 minutes, indicating iodobenzene.
Figure 11B:
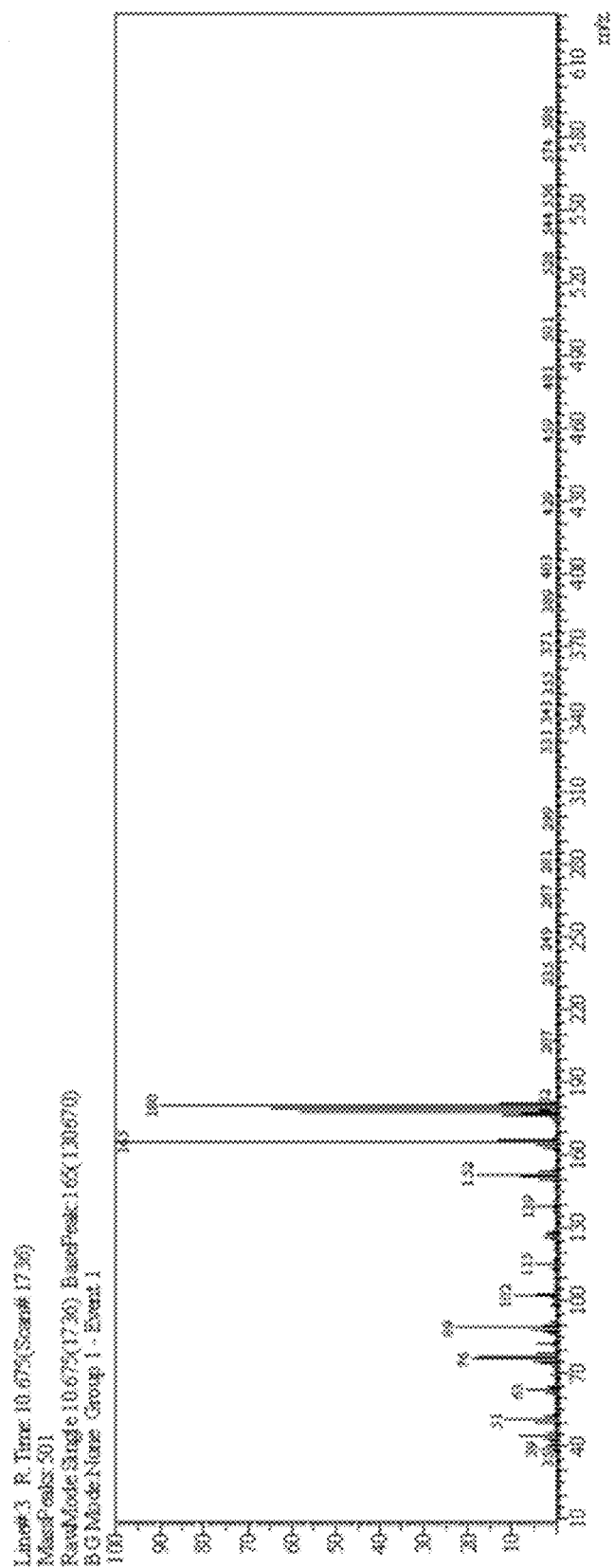
FIG. 11B shows a mass spectrum of GC peck from FIG. 10 at an R$_t$ of 10.675 minutes, indicating a configurational isomer of coupled product (minor product)
Figure 11C:
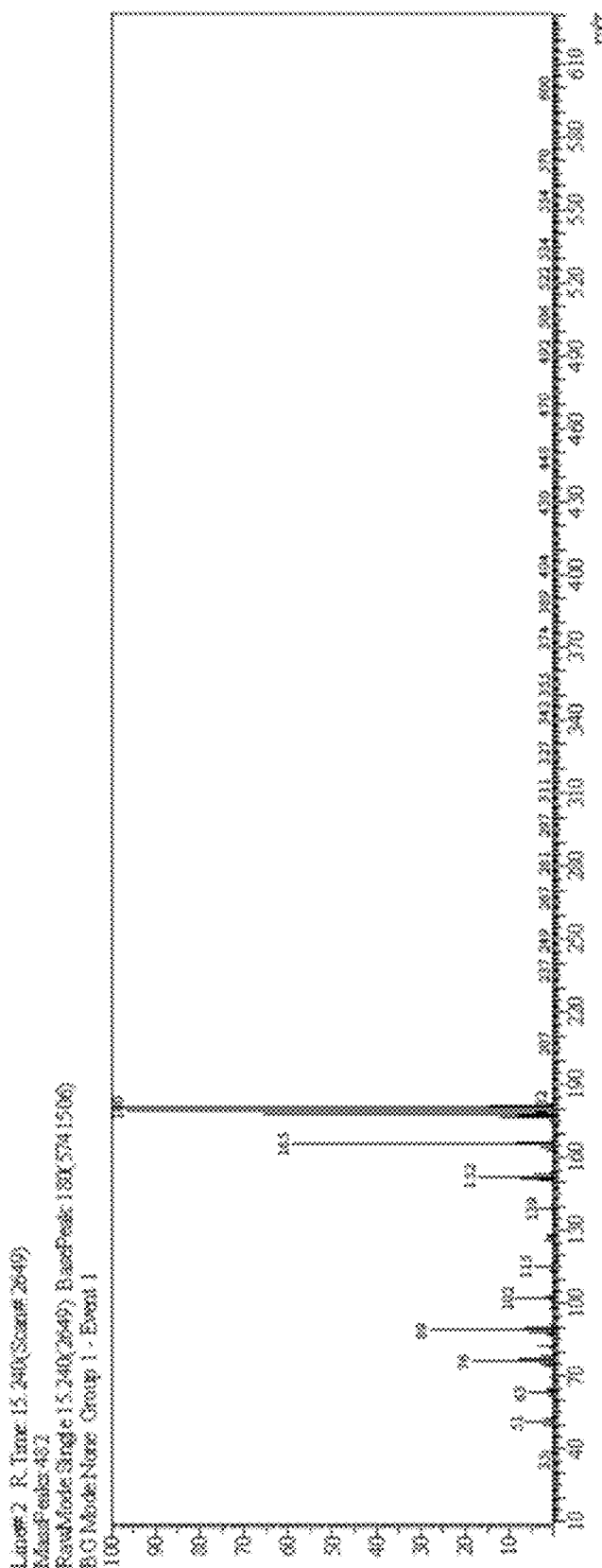
FIG. 11C shows a mass spectrum of GC peck from FIG. 10 at an R$_t$ of 15.240 minutes, indicating the major configurational isomer of coupled product from the reaction of styrene.

FIG. 10 shows a gas chromatograph (GC) of the results for a Mizoroki-Heck coupling reaction of styrene and iodobenzene, indicating peaks at 3.638, 10.651, and 15.238 minutes (most prominent). FIG. 11A shows a mass spectrum of the GC peak at an $R_t$ of 3.638 minutes, indicating unreacted iodobenzene. FIG. 11B shows a mass spectrum of the GC peak at an $R_t$ of 10.675, indicating a configurational isomer of coupled product, minor by-product. FIG. 11C shows a mass spectrum of the GC peak at an $R_t$ of 15.240 minutes, indicating the major configurational isomer of coupled product from the reaction of styrene.

Figure 12:
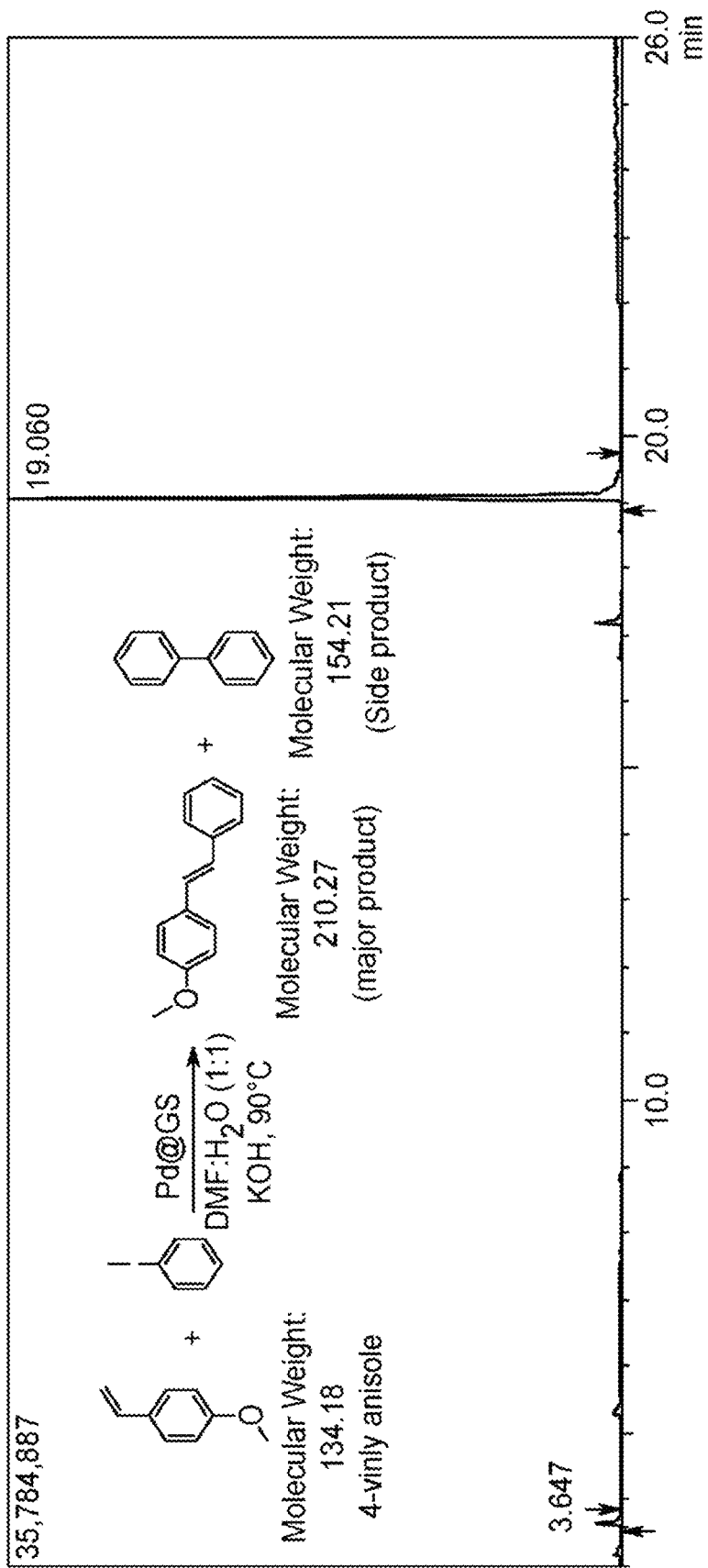
FIG. 12 shows a gas chromatography (GC) plot for a Mizoroki-Heck coupling reaction of 4-vinyl anisole and iodobenzene in the presence of an inventive catalyst.
Figure 13A:
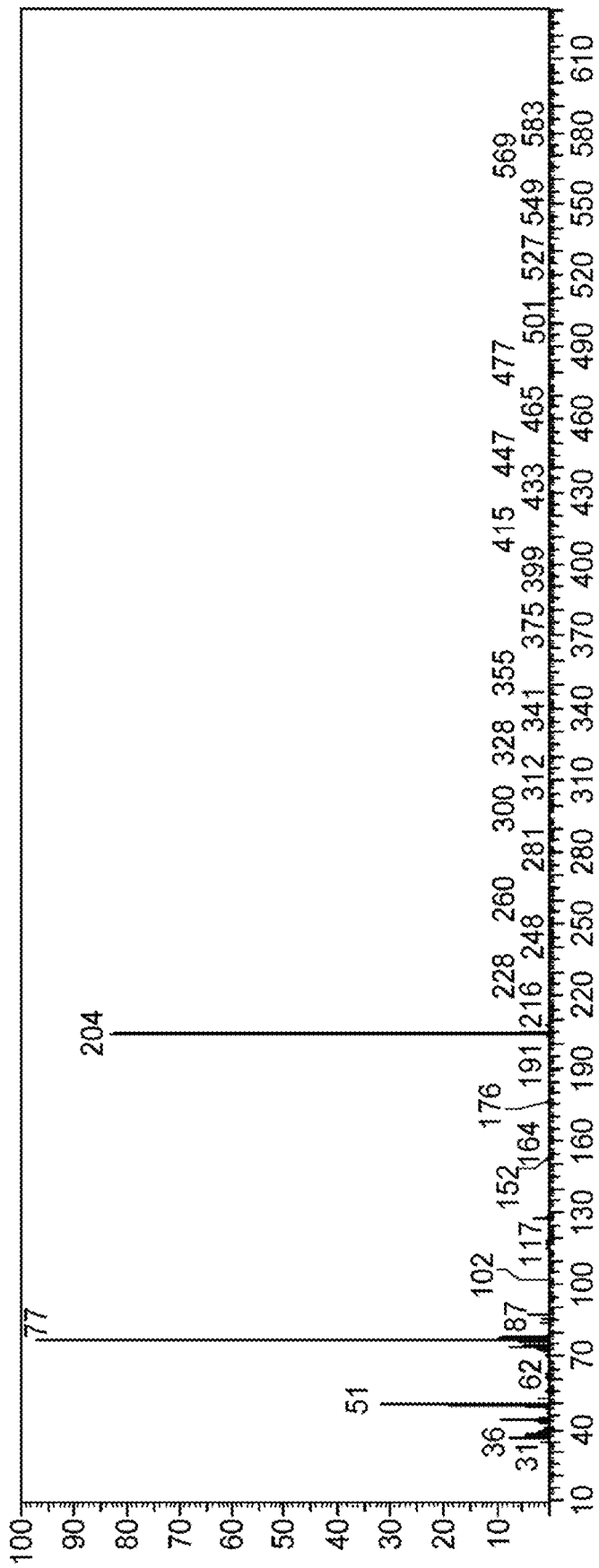
FIG. 13A shows a mass spectrum of GC peck from FIG. 12 at an R$_t$ of 3.660 minutes, indicating iodobenzene.
Figure 13B:
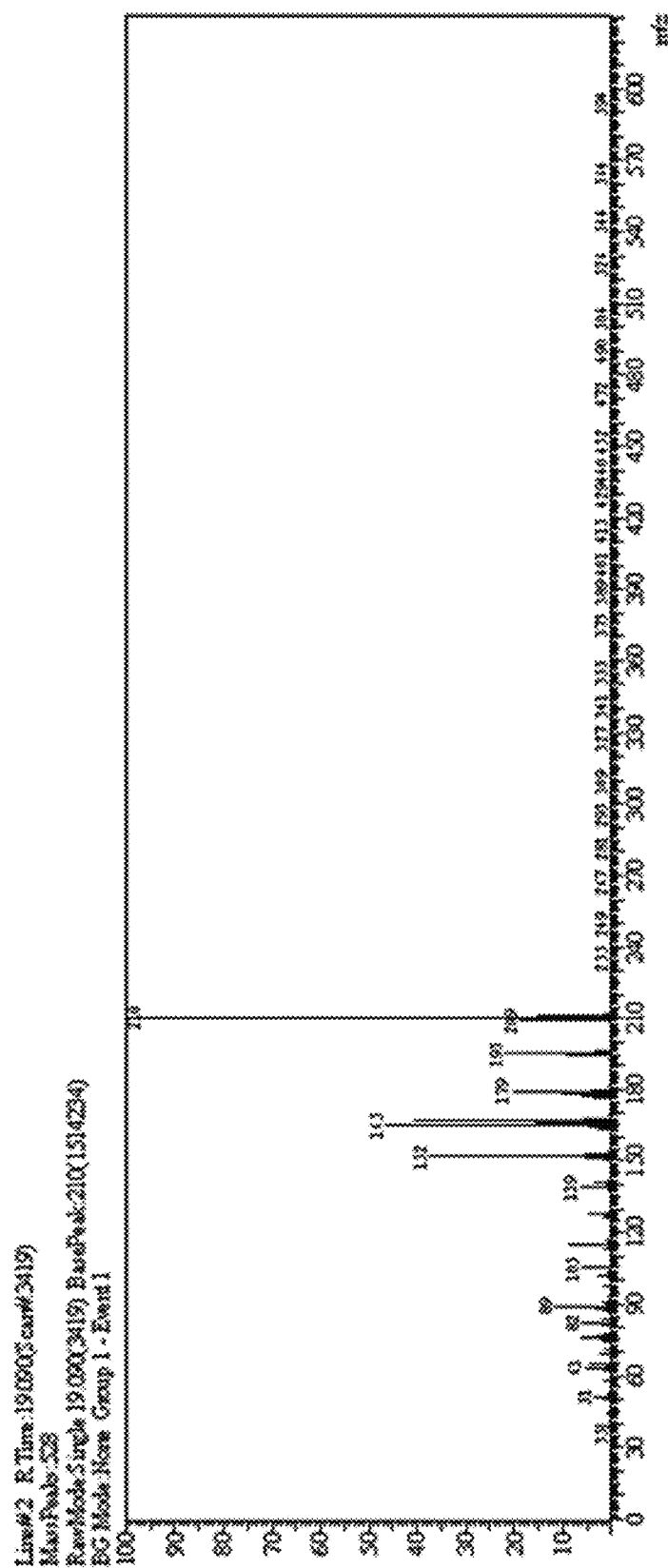
FIG. 13B shows a mass spectrum of GC peck from FIG. 12 at an R$_t$ of 19.09 minutes, indicating the coupled product from the reaction of 4-vinyl anisole.

FIG. 12 shows a gas chromatograph (GC) of the results for a Mizoroki-Heck coupling reaction of 4-vinyl anisole and iodobenzene, indicating peaks at 3.647 and 19.060 (most prominent). FIG. 13A shows a mass spectrum of the GC peak at an $R_t$ of 3.647 minutes, indicating unreacted iodobenzene. FIG. 13B shows a mass spectrum of the GC peak at an $R_t$ of 19.060 minutes, indicating the coupled product from the reaction of 4-vinyl anisole.

Figure 14A:
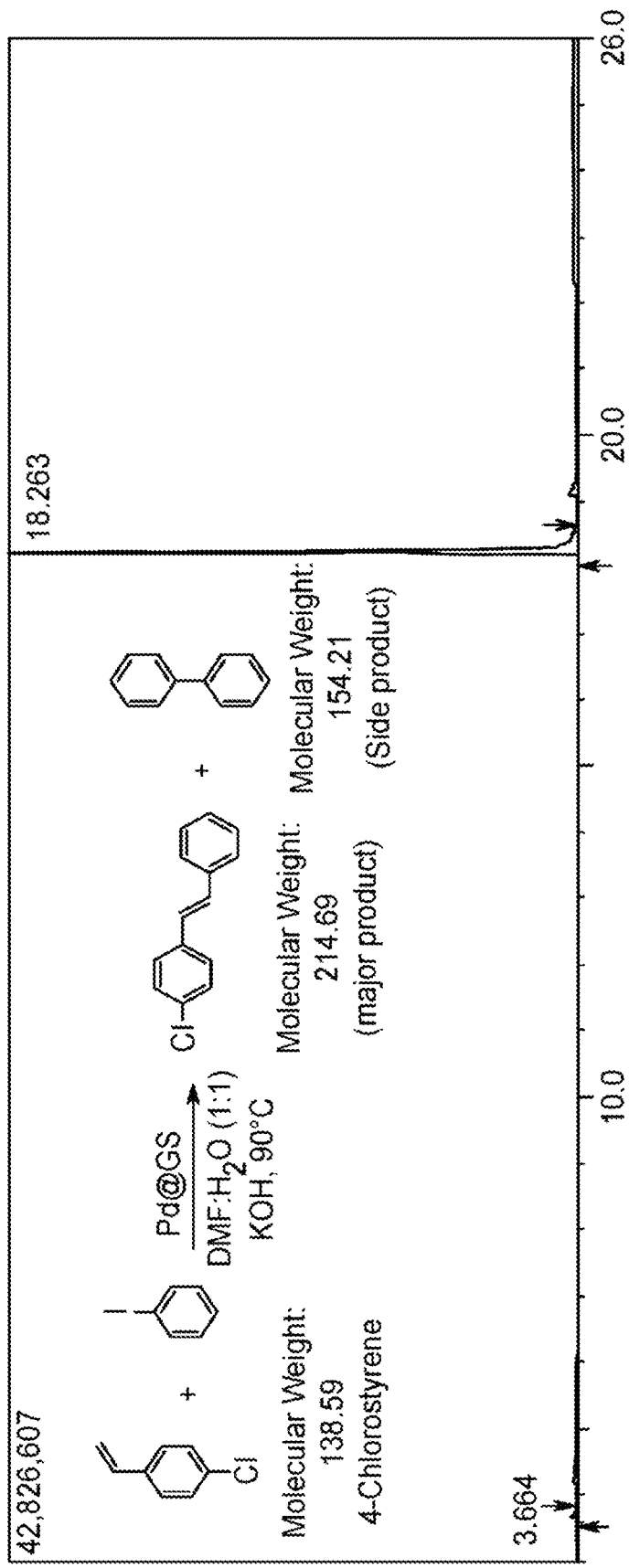
FIG. 14A shows a gas chromatography (GC) plot for a Mizoroki-Heck coupling reaction of 4-chlorostyrene and iodobenzene using an inventive catalyst.
Figure 14B:
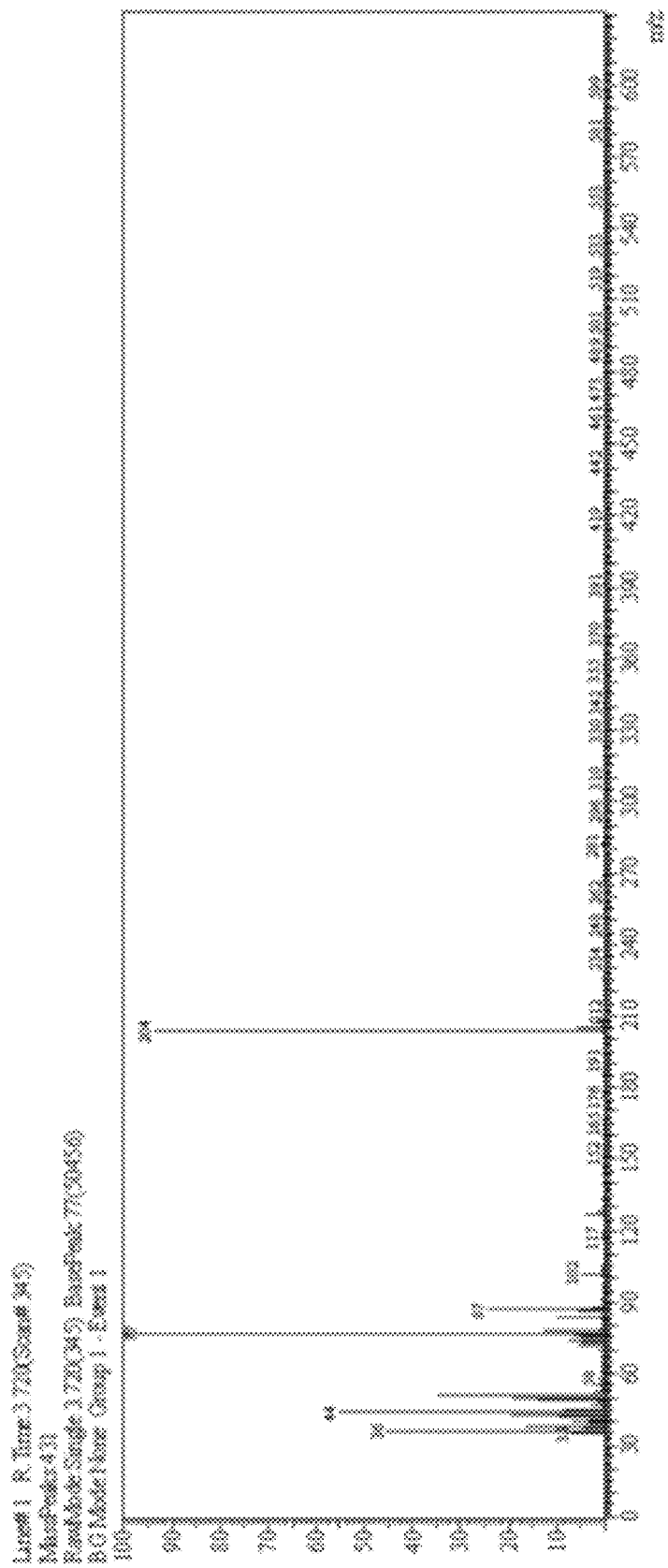
FIG. 14B shows a mass spectrum of GC peck from FIG. 14A at an R$_t$ of 3.720 minutes, indicating iodobenzene.
Figure 14C:
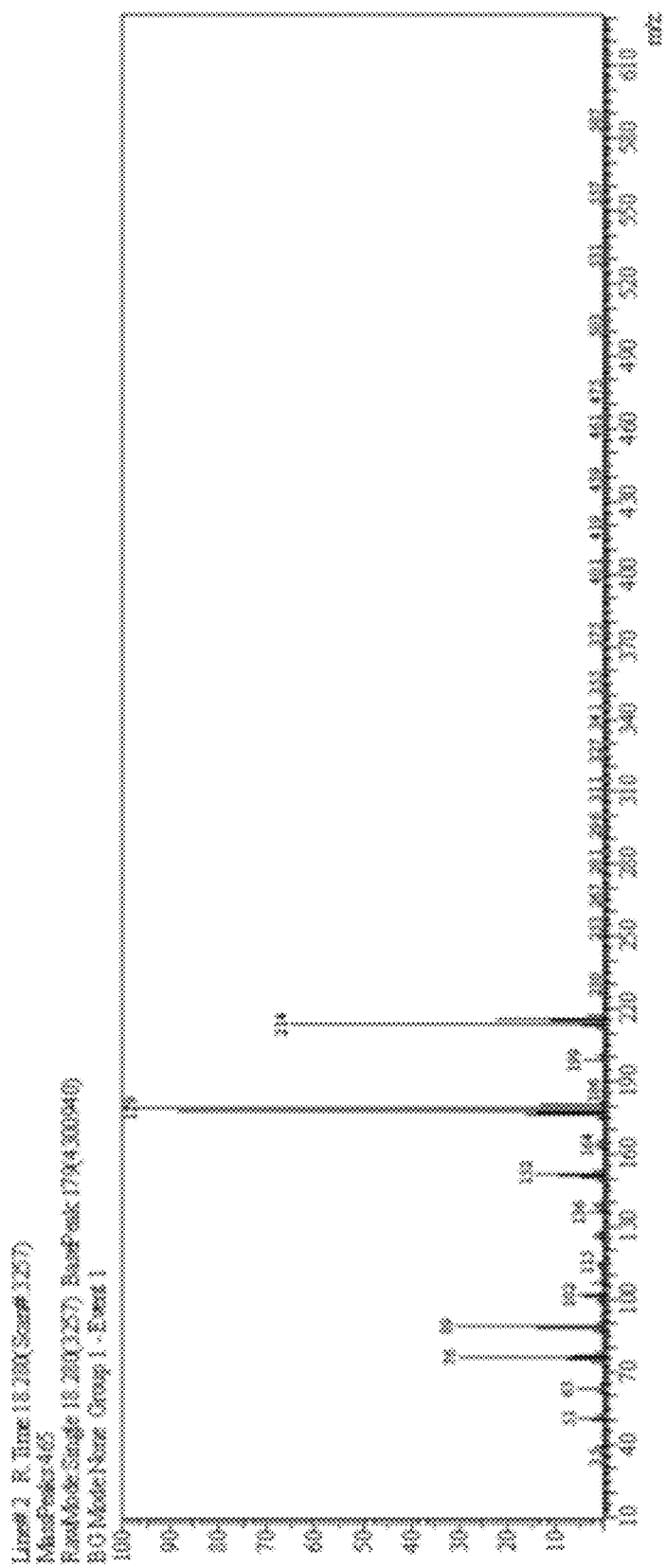
FIG. 14C shows a mass spectrum of GC peck from FIG. 14A at an R$_t$ of 18.28 minutes, indicating the coupling product of 4-chlorostyrene.

FIG. 14A shows a gas chromatograph (GC) of the results for a Mizoroki-Heck coupling reaction of analysis for the coupling reaction of 4-chlorostyrene and iodobenzene, indicating peaks at 3.664 and 18.263 minutes. FIG. 14B shows a mass spectrum of the GC peak at an $R_t$ of 3.664 minutes, indicating unreacted iodobenzene. FIG. 14C shows a mass spectrum of the GC peak at an $R_t$ of 18.263 minutes, indicating the coupling product of 4-chlorostyrene.

Figure 15A:
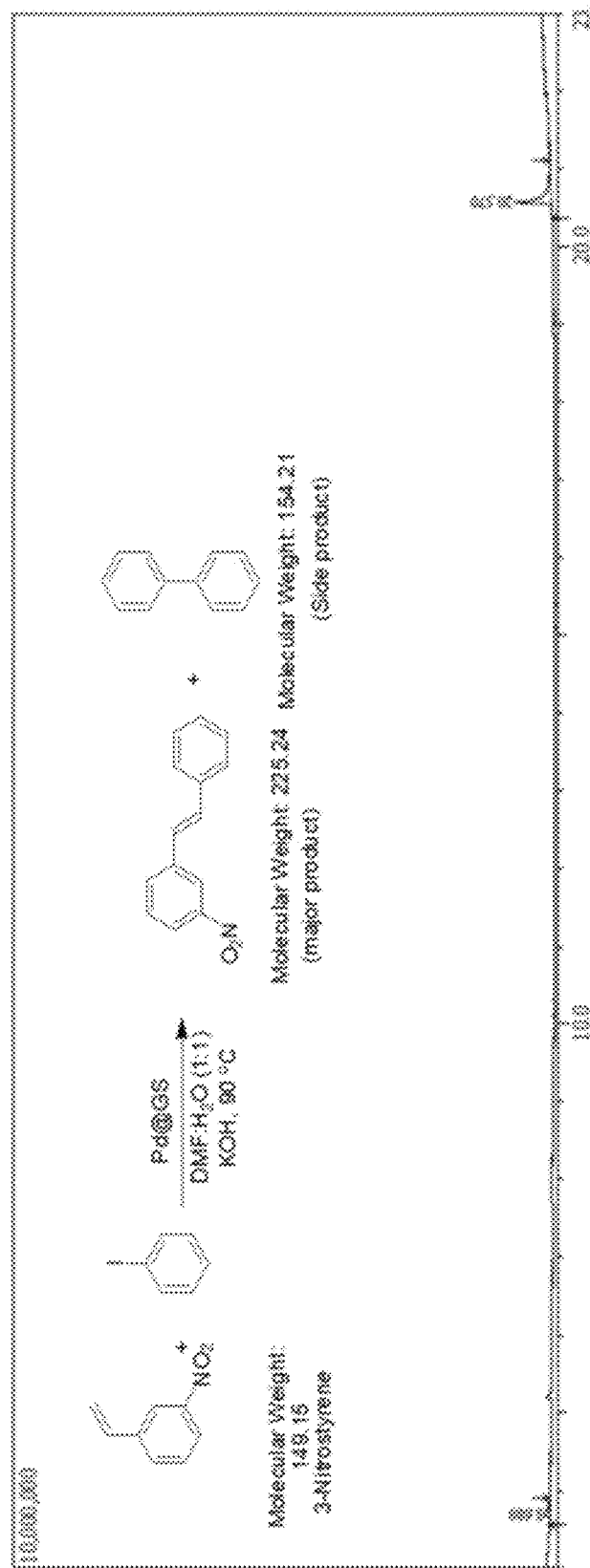
FIG. 15A shows a gas chromatography (GC) plot for a Mizoroki-Heck coupling reaction of 3-nitrostyrene and iodobenzene using an inventive catalyst.
Figure 15B:
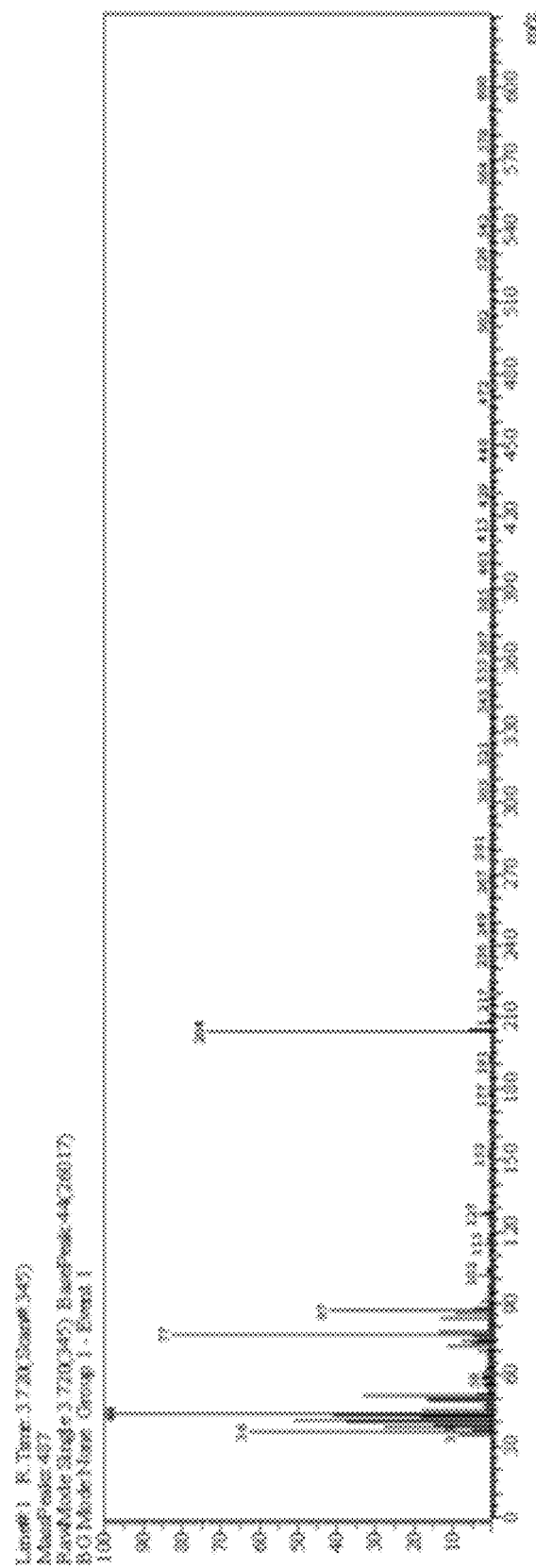
FIG. 15B shows a mass spectrum of GC peck from FIG. 15A at an R$_t$ of 3.720 minutes, indicating iodobenzene.
Figure 15C:
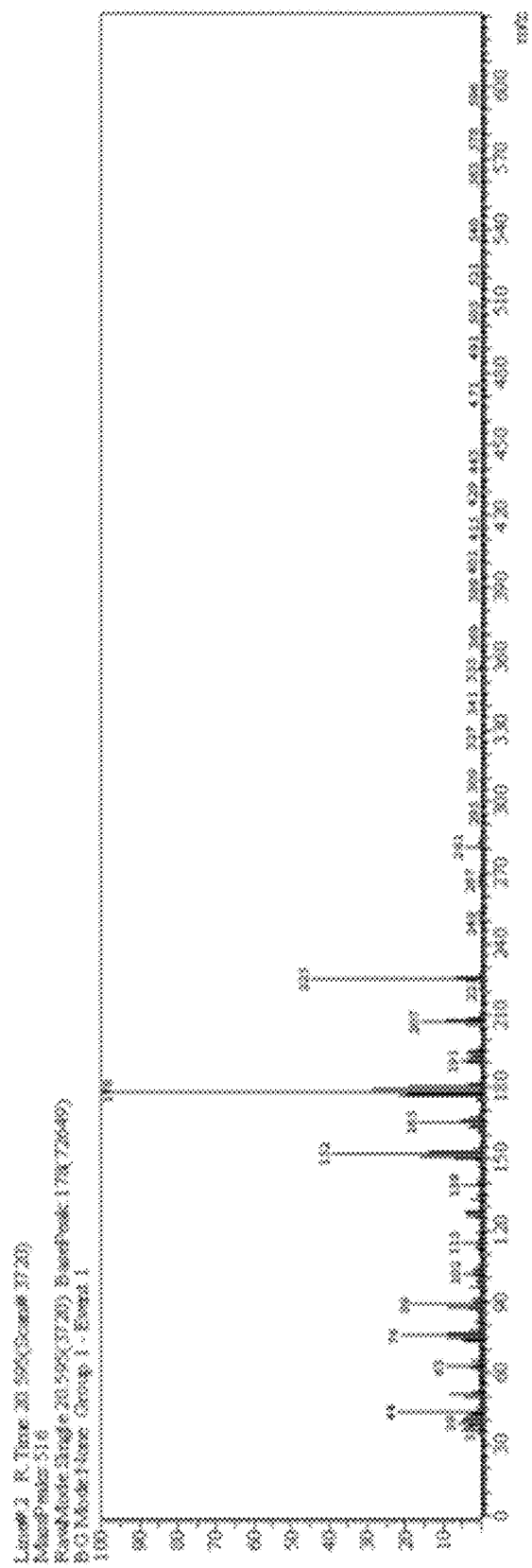
FIG. 15C shows a mass spectrum of GC peck from FIG. 15A at an R$_t$ of 20.57 minutes, indicating the coupling product of 3-nitrostyrene.

FIG. 15A shows a gas chromatograph (GC) of the results for a Mizoroki-Heck coupling reaction of analysis for the coupling reaction of 3-nitrostyrene and iodobenzene, indicating peaks at 3.668 and 20.570 minutes. FIG. 15B shows a mass spectrum of the GC peak at an $R_t$ of 3.668 minutes, indicating unreacted iodobenzene. FIG. 15C shows a mass spectrum of the GC peak at an $R_t$ of 20.570 minutes, indicating the coupling product of 3-nitrostyrene.

Figure 16A:
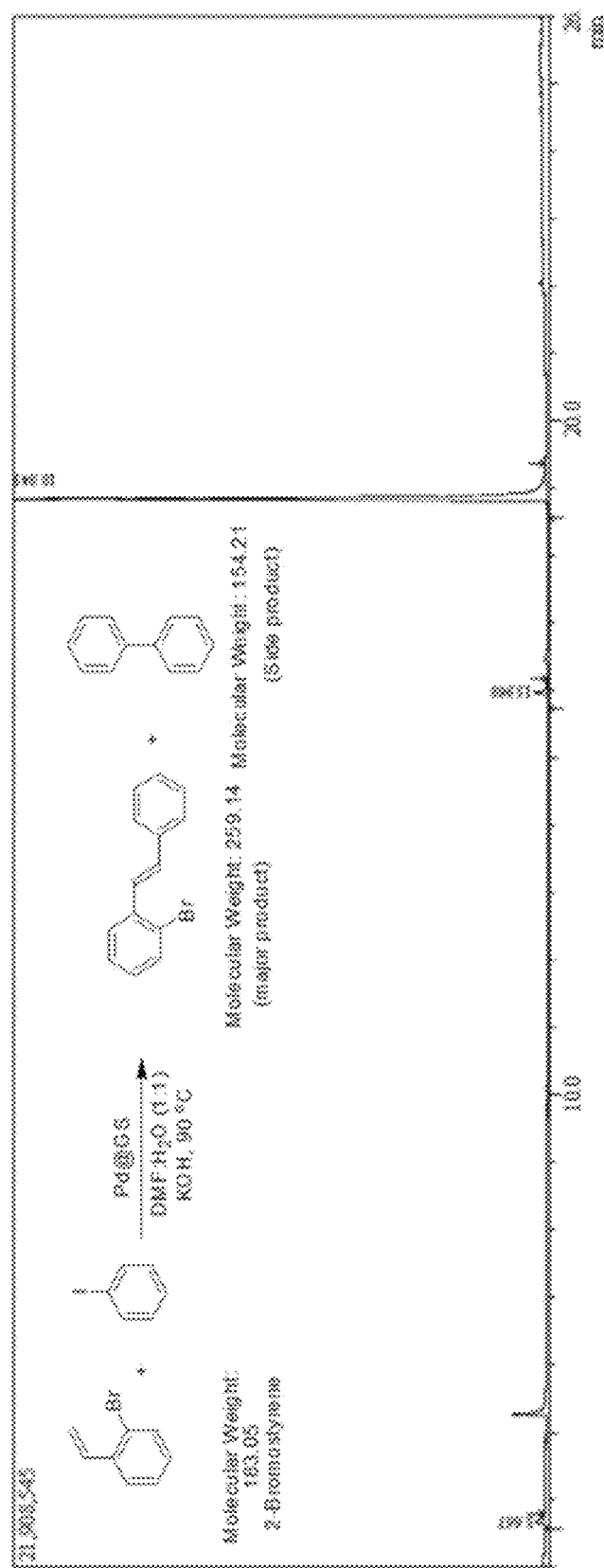
FIG. 16A shows a gas chromatography (GC) plot for a Mizoroki-Heck coupling reaction of 2-bromostyrene and iodobenzene using an inventive catalyst.
Figure 16B:
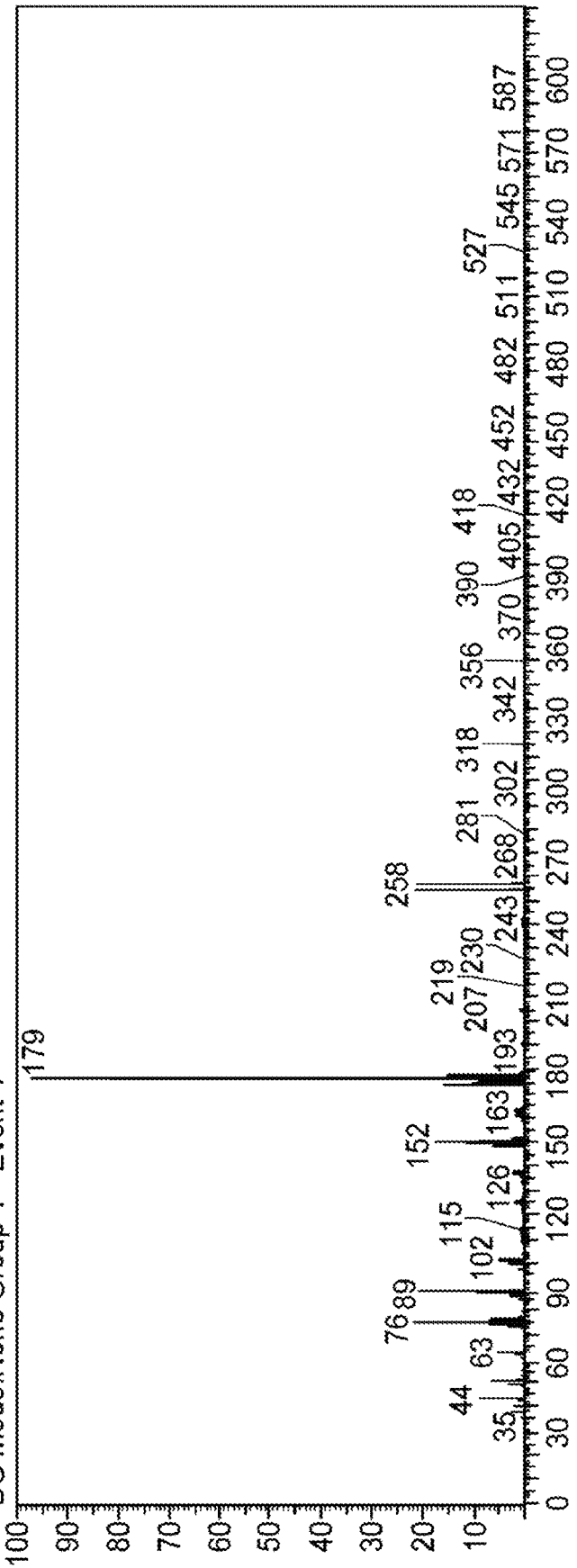
FIG. 16B shows a mass spectrum of GC peck from FIG. 16A at an R$_t$ of 15.970 minutes, indicating the isomer of the coupled product.
Figure 16C:
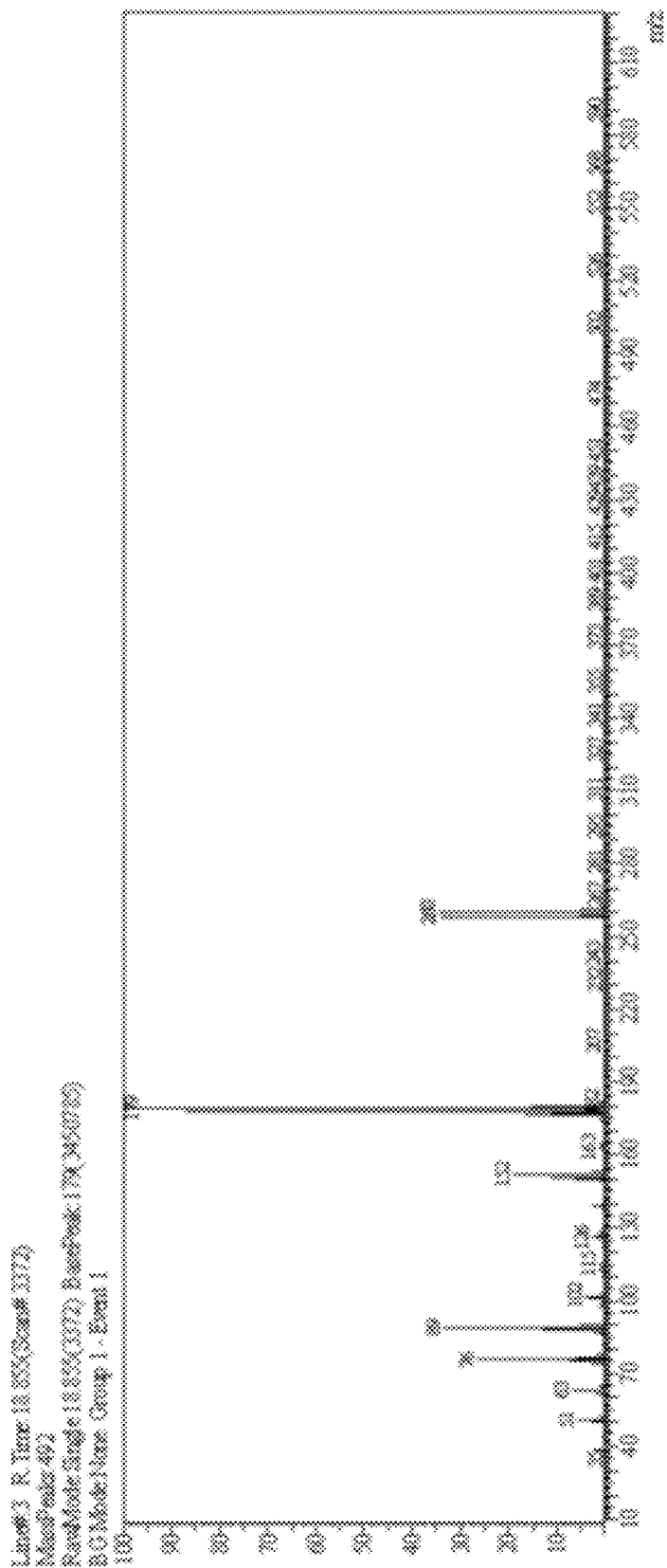
FIG. 16C shows a mass spectrum of GC peck from FIG. 16A at an R$_t$ of 18.845 minutes, indicating the coupling product of 2-bromostyrene.

FIG. 16A shows a gas chromatograph (GC) of the results for a Mizoroki-Heck coupling reaction of analysis for the coupling reaction of 2-bromostyrene and iodobenzene, indicating peaks at 3.667 and 18.845 minutes. FIG. 16B shows a mass spectrum of the GC peak at an $R_t$ of 3.667 minutes, indicating unreacted iodobenzene. FIG. 16C shows a mass spectrum of the GC peak at an $R_t$ of 18.845 minutes, indicating the coupling product of 2-bromostyrene.

Numerous modifications and variations of the present invention are possible in light of the above teachings. It is therefore to be understood that within the scope of the appended claims, the invention may be practiced otherwise than as specifically described herein.

The invention claimed is:

1. A method for making a natural material-supported palladium catalyst, the method comprising:
   mixing a particulate matrix, comprising jute strips comprising α-cellulose, hemicellulose, and lignin, with a palladium salt in an aqueous solution to form a suspension;
   combining the suspension with a borohydride reducing agent to form a mixture; and
   heating the mixture to thereby reduce at least 50 wt. % of the palladium salt, relative to total catalytic metal weight, and form a solid-supported palladium catalyst,
   wherein the particles of the particulate matrix have no average dimension less than 10 μm, and
   wherein the lignin is present in the particulate matrix in a range of from 15 to 30 wt. % relative to total particulate matrix weight.

2. The method of claim 1, wherein the reducing agent comprises a borohydride.

3. The method of claim 1, wherein the reducing agent comprises $NaBH_4$.

4. The method of claim 1, wherein the palladium salt comprises palladium ion comprises a $[PdCl_4]^{2-}$ anion.

5. The method of claim 1, wherein the heating comprises treating the mixture at a temperature in a range of from 40 to 100° C., and/or
   wherein the heating is conducted for a duration in the range of from 10 to 60 minutes.

6. The method of claim 1, wherein the particulate matrix comprises at least 75 wt. % of the α-cellulose, hemicellulose, and lignin, based on the total particulate matrix weight, and wherein palladium catalyst is disposed on the particulate matrix in an amount of from 0.01 to 1 wt. % relative to a total weight of the solid-supported palladium catalyst, and wherein the particulate matrix is in the form of particles, wherein the particles have an average longest dimension of at least 1 μm.

7. The method of claim 6, wherein the particles of the particulate matrix have no average dimension less than 100 μm.

8. The method of claim 6, wherein the palladium catalyst is in the form of nanospheres having an average particle size of from 2.5 to 45 nm.

9. The method of claim 8, wherein the average particle size of the nanospheres is from 5 to 15 nm.

10. The method of claim 6, wherein the particles of the particulate matrix comprise 20 to 60 wt. % α-cellulose, based on the total weight of the particulate matrix.

11. The method of claim 6, wherein the particles of the particulate matrix comprise 10 to 35 wt. % lignin, based on the total weight of the particulate matrix.

12. The method of claim 6, wherein the particles of the particulate matrix comprise 10 to 30 wt. % hemicellulose, based on the total weight of the particulate matrix.

13. The method of claim 6, wherein the particles of the particulate matrix comprise 30 to 50 wt. % α-cellulose, 15 to 30 wt. % lignin, and 15 to 25 wt. % hemicellulose, based on the total weight of the particulate matrix.

14. The method of claim 6, wherein the particles of the particulate matrix comprise at least 90 wt. % jute stems, based on the total weight of the particulate matrix.

15. The method of claim 6, wherein the palladium catalyst comprises at least 90 wt. % of palladium, relative to a total metal weight in the palladium catalyst.

* * * * *